United States Patent [19]
Soreq et al.

[11] Patent Number: 5,891,725
[45] Date of Patent: Apr. 6, 1999

[54] SYNTHETIC ANTISENSE OLIGODEOXYNUCLEOTIDES AND PHARMACEUTICAL COMPOSITIONS CONTAINING THEM

[75] Inventors: Hermona Soreq, Rishon Le Zion; Haim Zakut, Savyon, both of Israel; Fritz Eckstein, Gottingen, Germany

[73] Assignee: Yissum Research Development Co. of the Hebrew Univ. of Jerusalem, Jerusalem, Israel

[21] Appl. No.: 318,826

[22] PCT Filed: Apr. 15, 1993

[86] PCT No.: PCT/EP93/00911

§ 371 Date: Dec. 1, 1994

§ 102(e) Date: Dec. 1, 1994

[87] PCT Pub. No.: WO93/21202

PCT Pub. Date: Oct. 26, 1993

[30] Foreign Application Priority Data

Apr. 15, 1992 [IL] Israel .................................. 101600

[51] Int. Cl.$^6$ .............................. C07H 21/04; C12Q 1/68
[52] U.S. Cl. ........................... 435/372; 435/6; 435/91.1; 435/172.3; 435/325; 435/372; 435/375; 536/23.1; 536/24.31; 536/24.5; 514/44
[58] Field of Search ................................. 536/24.5, 23.1, 536/24.31, 24.33; 435/91.1, 6, 172.3, 240.2, 375, 377; 935/8, 34, 76, 78; 514/44

[56] References Cited

U.S. PATENT DOCUMENTS 5,225,326  7/1993  Bresser et al. ............................... 435/6

OTHER PUBLICATIONS

B. Monig et al., JBC, vol. 267(28) (Oct. 5, 1992) 19954–62.
E. Uhlmann et al., Chem. Rev. 90 (4) (Jun. 1990) 543–84.
P. Westermann et al., Biomed Biochim. Acta 48(1) ('89) 85–93.
W. James, Antiviral Chem. & Chemother. 2(4) ('91) 191–214.
J. Holt et al., Mol. Cell. Biol. 8(2) (Feb. 1988) 963–73.
D. Tidd, Anticancer Res. 10 ('90) 1169–82.
J. Milligan et al., J. Med. Chem. 36(14) (Jul. 9, 1993) 1923–37.
C. Stein et al, Science 261 (Aug. 20 1993) 1004–1012.
B. T. Seang et al., Cancer Gene Therapy 1(1) (Mar. 1994) 65–71.
J. Wetmer, Crit. Rev. in Biochem. Mol. Biol. 26(3/4) ('91) 227–59.
Baker et al., "Effects of oligo sequence and chemistry on the efficiency of oligodeoxyribonucleotide–mediated mRNA cleavage" *Nucleic Acids Research*, vol. 18, No. 12, p. 3537 (1990).
Caceres and Kosik, "Inhibition of neurite polarity . . . " *Nature*, 343:461–463 (1990).
Gnatt et al., "Expression of alternatively terminated unusual human butyrylcholinesterase messenger RNA transcripts . . . " *Cancer Research*, 50:1983–1987, (1990).
Iyer et al., "The automated synthesis of sulfur–containing oligodeoxyribonucletodies . . . " *J. Org. Chem.*, 55: 4693–4699 (1990).
Lapidot–Lifson et al., "Cloning and antisense oligodeoxynucleotide inhibition of a human homolog . . " *Proc. Natl. Acad. Sci., USA*, vol.89, pp. 579–583, (1992).
Lapidot–Lifson et al., "Coamplification of human acetylcholinesterase and butyrylcholinesterase genes in blood cells . . . " *Proc. Natl. Acad. Sci., USA*, vol. 86, pp. 4715–4719 (1989).
Layer et al., "Quantitative development and molecular forms of acetyl–and butyrylcholinesterase . . " *Journal of Neurochemistry*, 49:175–182 (1987).
Lee and Nurse, "Complementation used to clone a human homologue of the fission yeast cell cycle control gene cdc2" *Nature*, 327:31–35 (1987).
Loke et al., "Characterization of oligonucleotide transport into living cells" *Proc. Natl. Acad. Sci., USA*, 86:3474–3478 (1989).
Malinger et al., "Cholinoceptive properties of human primordial, preantral, and antral oocytes. . " *J. Mol. Neurosci.*, 1:77–84 (1989).

(List continued on next page.)

*Primary Examiner*—John L. LeGuyader
*Attorney, Agent, or Firm*—Kohn & Associates

[57] ABSTRACT

The invention relates to synthetic phosphorothioated or partially phosphorothioated oligodeoxynucleotides capable of selectively modulating hemopoietic bone marrow cells development. More particularly, the invention relates to synthetic antisense oligodeoxynucleotides directed against a region spanning the AUG initiation condon in human ACHE or 2HS genes, having phosphorothioate bonds linking between the nucleotide bases; synthetic antisense oligodeoxynucleotides directed against a region spanning the AUG initiation condon in human ACHE gene, 2HS gene or BCHE gene or against a 5'-region in the human CHED (cdc2 homolog) gene, having phosphorothioate bonds linking between the four 3'-terminus nucleotide bases. The invention also relates to pharmaceutical compositions comprising as active ingredient at least one synthetic phosphorothioated or partially phosphorothioated antisense oligodeoxynucleotides according to the invention in physiologically acceptable carrier in diluent. The antisense oligodeoxynucleotides of the invention and the pharmaceutical compositions containing them are suitable for inhibiting abnormal hemopoietic cells proliferation, inhibiting abnormal platelet proliferation, increasing stem cell fraction in bone marrow cell cultures, enhancing macrophage production and increasing stem cells counts, reducing immune response of organs to be transplanted, suppressing immune response of a recipient of an allotransplanted organ, and arresting growth of malignant tumors.

11 Claims, 15 Drawing Sheets

OTHER PUBLICATIONS

Agarwal et al., "Pharmacokinetics, biodistribution, and stability of oligodeoxynucleotide phosphorothioates in mice" *Proc. Natl. Acad. Sci. USA*, 88:7595–7599 (1991).

Akhtar et al., "Interactions of antisense DNA oligonucleotide analogs with phospholipid membranes (liposomes)" *Nucleic Acids Research*, vol. 19, No. 20 pp. 5551–5559 (1991).

Moffat, "Making sense of antisense" *Science*, 253:510 (1991).

Morrison, "Suppression of basic fibroblast growth factor expression by antisense oligodeoxynucleotides . . ." *J. Biol. Chem.*, 266:728 (1991).

Owens and Bunge, "Schwann cells infected with a recombinant retrovirus expressing myelin–associated glycoprotein . . ." *Neuron*, 7:565–575 (1991).

Patinkin et al., "Manipulations of cholinesterase gene expression modulate murine megakaryocytopoiesis in vitro" *Molecular and Cellular Biology*, 10:6046–6050 (1990).

Pieken et al., "Kinetic characterization of ribonuclease–resistant 2'–modified hammerhead ribozymes" *Science*, 253:314 (1991).

Prody et al., "Isolation and characterization of full–length cDNA clones coding for cholinesterase from fetal human tissues" *Proc. Natl. Acad. Sci. USA*, 84:3555–3559 (1987).

Rakonczay and Brimijoin, "Biochemistry and pathophysiology of the molecular forms of cholinesterases" in *Subcellular Biochemistry*, edited by J.R. Harris, Plenum Publishing, vol. 12, p. 335 (1988).

Shaw et al., "Modified deoxyoligonucleotides stable to exonuclease degradation in serum" *Nucleic Acids Research*, 19:747–750 (1991).

Soreq et al., "Molecular cloning and construction of the coding region for human acetylcholinesterase . . ." *Proc. Natl. Acad. Sci. USA*, 87:9688–9692 (1990).

Soreq et al., "Expression and tissue–specific assembly of human butyrylcholine esterase . . ." *J. Biol. Chem.*, 264:10608–10613 (1989).

Weinstein et al., "Suppression by antisense mRNA demonstrates a requirement for the glial fibrillary acidic protein" *J. Cell. Biol.*, 112:1205 (1991).

Whitesell et al., "Episome–generated n–myc antisense RNA restricts the differentiation potential . . ." *Molecular and Cellular Biology*, 11:1360–1371 (1991).

Woolf et al., "The stability, toxicity and effectiveness of unmodified and phosphorothioate antisense oligodeoxynucleotides . . ." *Nucleic Acids Research*, 18:1763 (1990).

Yakubov et al., Mechanism of oligonucleotide uptake by cells: involvement of specific receptors? *Proc. Natl. Acad. Sci. USA*, 86:6454–6458 (1989).

Blake et al., "Hybridization arrest of globin synthesis in rabbit riticulocyte lysates and cells . . ." *Biochem.*, 24:6139–6145 (1985).

Burstein et al., "Quantitation of megakaryocytopoiesis in liquid culture by enzymatic determination of acetylcholinesterase" *J. Cell. Physiol.*, 122:159–165 (1985).

Burstein et al., "Megakaryocytopoiesis in culture: modulation by cholinergic mechanisms" *J. Cell. Physiol.*, 103:201–208 (1980).

Calabretta et al., "Normal and leukemic hematopoietic cells manifest differential sensitivity to inhibitory effects of c–myb antisense . . ." *Proc.Natl.Acad.Sci.USA*, 88:2351–2355 (1991).

Chiang et al., "Antisense oligonucleotides inhibit intercellular adhesion molecule 1 expression . . ." *J. Biol. Chem.*, 266:18162–18171 (1991).

Cooney et al., "Site–specific oligonucleotide binding represses transcription of the human c–myc gene in vitro" *Science*, 241:456 (1988).

Eckstein, "Nucleoside phosphorothioates" *Ann.Rev.Biochem.*, 54:367–402 (1985).

Eguchi, "Antisense RNA" *Ann.Rev.Biochem.*, 60:631–52 (1991).

Galileo et al., "Retrovirally introduced antisense integrin RNA inhibits neuroblast migration in vivo" *Neuron*, 9:1117–1131 (1992).

Haseloff and Gerlach, "Simple RNA enzymes with new and highly specific endoribonuclease activities" *Nature*, 334:585–591 (1988).

Layer and Sporns, "Spatiotemperoal relationship of embryonic cholinesterases with cell proliferation in chicken . . ." *Proc.Natl.Acad.Sci.USA*, 84:284–288 (1987).

Leonetti et al., "Intracellular distribution of microinjected antisense oligonucleotides" *Proc.Natl.Acad.Sci.USA*, 88:2702–2706 (1991).

Moffat, "Making sense of antisense" *Science*, 253:510–511 (1991).

Moffat, "Triplex DNA finally comes of age" *Science*, 252:1374–1375 (1991).

Moreno and Nurse, "Substrates for p34$^{cdc2}$: in vivo veritas?" *Cell*, 61:549–551 (1990).

Nielsen et al., "Sequence–selective recognition of DNA by strand displacement with a thymine–substituted polyamide" *Science*, 254:1497–1500 (1991).

Rangini et al., "CHox E, a chicken homeogene of the H2.0 type exhibits dorso–ventral restriction . . ." *Mechanisms of Development*, 35:13–24 (1991).

Sarver et al., "Ribozymes as potential anti–HIV–1 therapeutic agents" *Science*, 247:1222–1225 (1990).

Spitzer and Eckstein, "Inhibition of deoxyribonucleases by phosphorothioate groups in oligodeoxyribonucleotides" *Nucleic Acids Res.*, 16:11691–11704 (1988).

Szczylik et al., "Selective inhibition of leukemia cell proliferation by BCR–ABL antisense oligodeoxynucleotides" *Science*, 253:562–565 (1991).

Wilkinson et al., "Expression of the proto–oncogene int–1 is restricted to specific neural cells . . ." *Cell*, 50:79–88 (1987).

| | Oligodeoxythionucleotide | | | | | |
|---|---|---|---|---|---|---|
| Property | S-BCHE | AS-BCHE | AS-2Hs | AS-CHED | AS-ACHE | S-ACHE |
| Tm,°C | 61.9 | 61.9 | 55.3 | 69.8 | 82.1 | 82.1 |
| A,% | 40 | 20 | 27 | 13 | 7 | 20 |
| T,% | 20 | 40 | 40 | 40 | 20 | 7 |
| G,% | 20 | 20 | 33 | 7 | 40 | 33 |
| C,% | 20 | 20 | 20 | 40 | 33 | 40 |
| 3'Seq. | AGTC | GCAT | CCAT | CCAT | TCAT | GCAG |
| dimer formation | 5'ATGCAT TACGTA5' | 5'ATGCAT TACGTA5' | 5'---TATA ATAT---5' | — | 5'---G-GGCC-C3' 3'C-CCGG-G5' | |
| Dimer Kcal/mol | -4.9 | -4.9 | +1.8 | — | -4.3 | -4.3 |
| Total loops | 19 bonds | 5 bonds | 14 bonds | — | 11 bonds | 11 bonds |
| 3' Hyb. | — | 1op, 5 bonds | 3op, 11 bonds | — | 20p.,17 bonds | 20p.,11 bonds |
| Options | 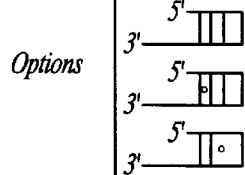 |  | 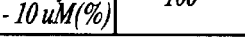 | — |  | 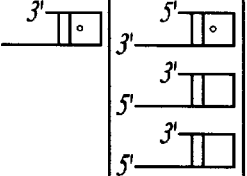 |
| toxicity at 5-10 uM(%) | 100 | 72 | 62 | 22 | ND | ND |
Fig-4

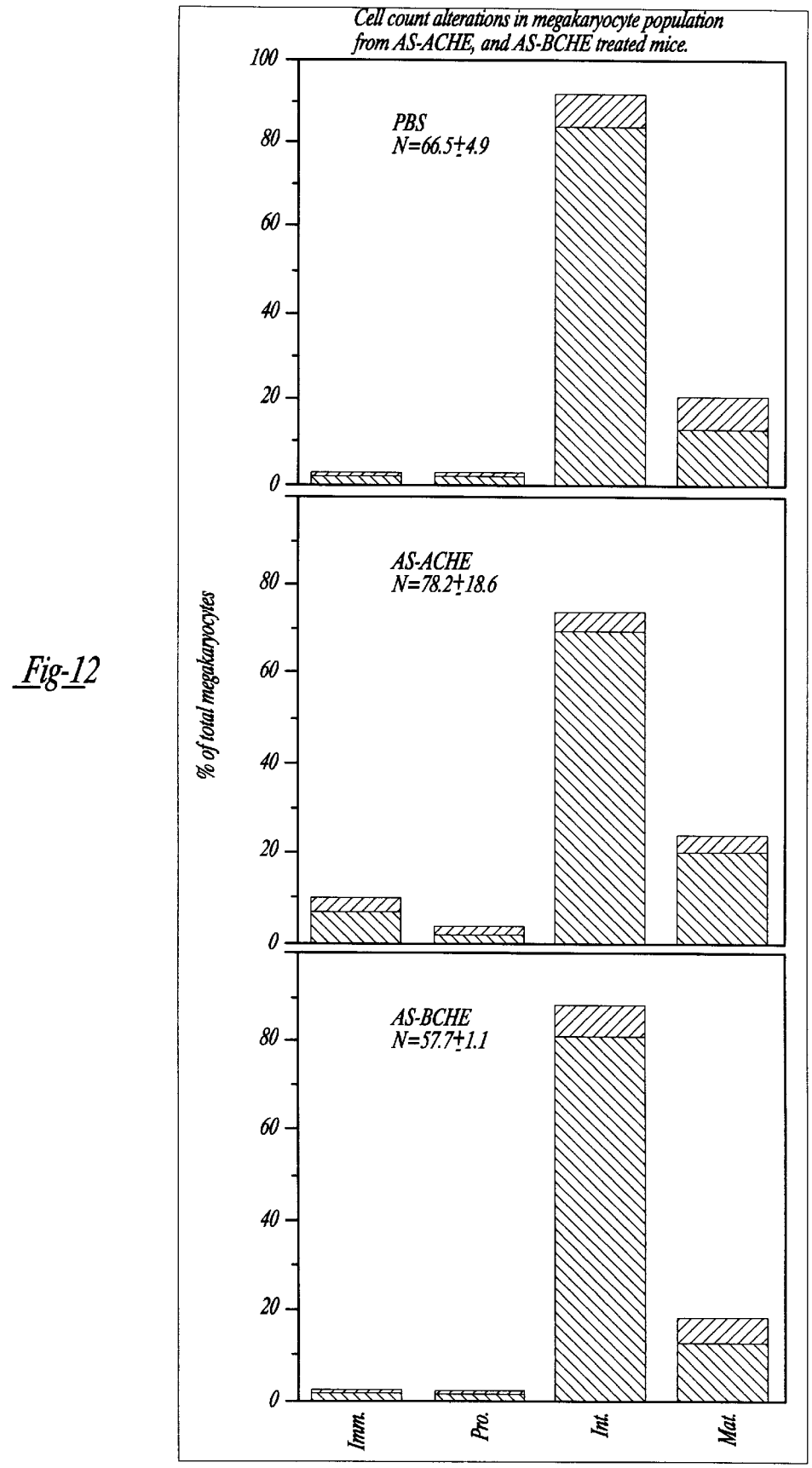

SYNTHETIC ANTISENSE OLIGODEOXYNUCLEOTIDES AND PHARMACEUTICAL COMPOSITIONS CONTAINING THEM

This application is a 371 of PCT/EP93/00911, filed Apr. 15, 1993.

BACKGROUND OF THE INVENTION

The BCHE and ACHE genes encoding the acetylcholine hydrolyzing enzymes butyrylcholinesterase (BuChE, EC 3.1.1.8) and actylcholinesterase (AChE, EC 3.1.1.7) are expressed in various developing cell types, including embryonic [Layer, P. G. and Sporns, O., Proc. Natl. Acad. Sci. USA 84:284–288 (1987)], hematopoietic [Burstein, S. A., et al., J. Cell Physiol. 122:159–165 (1985)] and germ cells [Johnson, C. D., et al., Neuron 1:165–173 (1988); Malinger, G., et al., Mol. Neurosci. 1:77–84 (1989)].

Both AChE and BuChE include the peptide motif S/T-P-X-Z, which makes-them potential substrates for phosphorylation by cdc2 kinases, the general controllers of the cell cycle [Lapidot-Lifson, Y., et al., Proc. Natl. Acad. Sci., USA 89: 579–583 (1992)]. Most other substrates of cdc2 kinases perform biological functions necessary for cell cycle-related processes [Moreno, S. and Nurse, P., Cell 61:549–551 (1990)]. Thus, interference with either CHE or cdc2 transcription processes may be expected to divert and/or arrest cell division, and controlling these processes can be useful for several, medically important, procedures.

Biochemical and histochemical analyses indicate that both AChE and BuChE are expressed, in high levels, in various fetal tissues of multiple eukaryotic species [Rakonczay, Z., et al., Subcellular Biochemistry 12:335–378, Harris, J. R., Ed., Plenum Press, N.Y. (1988)], where cholinesterases (ChEs) are coordinately regulated with respect to cell proliferation and differentiation [Layer, P. G., et al., Neurochem. 49:175–182 (1987)]. The specific role to be attributed to ChEs in embryonic development may hence be related with cell division, so that their biological function(s) in these tissues are tentatively implicated in the control of organogenesis.

In addition to its presence in the membranes of mature erythrocytes, AChE is also intensively produced in developing blood cells in vivo [Paulus, J. P., et al., Blood 58:1100–1106 (1981)] and in vitro [Burstein, S. A., et al., J. Cell Physiol. 103:201–208 (1980)] and its activity serves as an acceptable marker for developing mouse megakaryocytes [Burs- tein (1985) ibid.]. Furthermore, administration of acetyl- choline analogues as well as cholinesterase inhibitors has been shown to induce megakaryocytopoiesis and increased platelet counts in the mouse [Burstein, S. A., et al., Clin. Haematol. 12:3–27 (1983)], implicating this enzyme in the commitment and development of these haematopoietic cells.

The DNAs coding for human BuChE and AChE have been cloned [Prody, C., et al., Proc. Natl. Acad. Sci., USA 86:3555–3559 (1987); Soreq et al., Proc. Natl. Acad. Sci., USA 87:9688–9692 (1990)] and the human CHEl locus has been mapped [Gnatt, A., et al., Cancer Res. 50:1983–1987 (1990)] to the 3q26-ter chromosomal domain that is subject to aberrations in leukemias accompanied by abnormal megakaryocytopoiesis and platelet counts [Pintado, T., et al., Cancer 55:535–541 (1985)]. Co-amplification of the ACHE and BCHE genes was subsequently observed in leukemias and platelet disorders [Lapidot-Lifson, Y., et al., Proc. Natl. Acad. Sci., USA 4715–4717 (1989); Zakut, H., et al., Mutation Research, in press (1992)]. The hemopoietic system thus appears to be subject to developmental control as affected by the expression of the ChEs.

Inhibition of the expression of developmentally important genes should, in principle, divert developmental processes to directions which are not dependent on the expression of these genes. One useful approach to affect such developmental processes is based on "antisense" technology. The use of oligonucleotides to intervene in the genetic processes of the cell bears an important therapeutic potential. Thus, "informational drugs" with possible clinical applications are being developed which arrest the expression of cloned genes. The hematopoietic system may be the first logical target for novel therapy protocols based on the recent achievement in genetic engineering, since it includes proliferating stem cells and because of its extreme sensitivity to external stimuli [Wilson, J. D., et al., Harrison's Principles of Internal Medicine, 12th Ed., McGraw-Hill, Inc., New York, Chapters 268–269; 285–288 (1991)]. Stem cells may be defined as cells which can replicate repeatedly and differentiate into various kinds of committed cells. Commitment will gradually limit the differentiation choices for cells in which it occurs, until precursor cells are formed with only one choice (i.e. erythrocytes, megakaryocytes or macrophages). The first stem cells can thus be defined as totipotent, i.e. they may make all of the choices in the blood and immune system. The orientation of such cells into desired direction should be most useful in overcoming undesired changes, such as depletion or excess of specific subpopulations of hemopoietic cells. Less, although also useful is the redirection of the more limited pluripotent stem cells. Stem cells account for $\leq 0.1\%$ of cells in bone marrow. They can be detected either directly, by immunocytochemical methods, or retroactively, by cell culture growth and subsequent evaluation of formed colonies. For therapeutic purposes, it would be desirable to control stem cells differentiation and cause totipotent and pluripotent stem cells to replicate.

Production rate of bone marrow cells in healthy individuals may reach $10^{10}$ platelets and differentiated blood cells per hour. Life span of these cells varies from years for some lymphocytes, 120 days for erythrocytes to 10 days for platelets and 10 hours for neutrophils. Changes in the subpopulations of hemopoietic stem cells may be found in patients suffering malignant myeloproliferative diseases, such as various leukemias etc., in blood cells proliferative diseases such as polycythemia vera etc., and in autoimmune diseases like lupus erythomatosus etc., in which the blood production system is defective. Defective hemopoiesis is further observed in patients undergoing various commonly used therapeutical treatments like chemotherapy and irradiation which impair the blood production system. Thus all cancer patients, individuals following tissue transplantation and others who have suffered poisoning by chemicals and/or different drugs, display abnormal hemopoiesis with its subsequent consequences. The therapeutical value of the ability to modulate hemopoietic cell division in patients suffering any of the above pathological conditions is self-evident. Furthermore, modulation of hemopoietic cell division, and especially increasing the number of hemopoietic stem cells, may be of particular advantage for the clinical procedure of bone marrow transplantation. Techniques are already available for freezing bone marrow cells and for their subsequent transplantation in patients suffering any of the above pathological conditions. However, the only transplanted bone marrow cells which can survive in the recipient and proliferate to improve his/hers condition are stem cells. The above procedure may be autotransplantation, using the recipient's own bone marrow, or allotransplantation, using bone marrow from a compatible donor.

As mentioned above, cholinergic signals are implicated in the commitment and development of haematopoietic cells. Recently, preliminary evaluation of antisense oligonucleotides incorporation in vivo was performed which revealed the short term therapeutic applicability of this approach [Cohen, et al., Antisense Res. & Dev. 2:191 (1991)]. Antisense oligonucleotides of 15–20 bases are usually long enough to ascertain that they will only have one complementary sequence in the mammalian genome. In addition, they hybridize well with their target mRNA [Cohen et al., ibid.]. Modification of the phosphodiester backbone renders these oligonucleotides resistant to degradation by nucleases [Spitzer, F. and Eckstein, F., Nuc. Ac. Res. 16: 11691–11704 (1988)]. Both methylphosphonate and phosphorothioate groups were used for this purpose [Baker, C., et al., Nuc. Ac. Res. 18:3537 (1990)]. Being nonionic, the methylphosphonate analogs were predicted to exhibit increased cellular uptake [Blake, et al., Biochem. 24:6139 (1985)]. However, antisense methylphosphonate oligomers were shown to be incapable of inhibiting N-ras expression in vitro [Tidd, et al., Anti-Cancer Drug Design 3:117 (1988)] whereas the in vitro translation of several oncogene mRNAs was successfully blocked by phosphodiester and/or phosphorothioate antisense oligonucleotides [c-myc: McManaway et al., Lancet 335:808 (1990), Watson et al., Cancer Res. 51:3996 (1991); bcl-2: Reed et al., Cancer Res. 50:6565 (1990); myb: Calabrett et al., Proc. Natl. Acad. Sci. USA 88:2351 (1991); bcr-ab: Szczylik et al., Science 253:562 (1991)]. Both sense and nonsense oligonucleotides served as controls in these studies and were shown to be non-effective, while antisense oligonucleotides selectively inhibited their target gene expression and phosphorothioate oligonucleotides were more potent because of their greater stability [Woolf, T. M., et al., Nuc. Ac. Res. 18:1763 (1990)3.

Antisense oligonucleotides are able to interfere specifically with synthesis of the target protein of interest [Moffat, Science 253:510 (1991)]. This may occur by inhibition of polysome formation and/or functioning, according to the position of the antisense oligonucleotide within the target mRNA. Thus, the frequent choice of the sequence surrounding the translation initiation codon as target for antisense oligonucleotide inhibition aims to prevent the formation of the initiation complex. Indeed, antisense RNAs occur naturally as regulators of translation [Eguchi et al., Ann. Rev. Biochem. 60:631 (1991)]. Other mechanisms of antisense oligonucleotide inhibition involve activation of ribonuclease H, which subsequently performs digestion of the antisense oligonucleotide-mRNA hybrids [Chiang, M. Y., et al., J. Biol. Chem. 266:18162 (1991)], or interference with splicing through antisense oligonucleotides targeted to mRNA splice sites [Kole et al., Adv. Drug Deliv. Rev. 6:271 (1991)].

In addition to their mRNA targets, antisense oligonucleotides are also complementary to the genomic sequences expressing these mRNAs. When injected into cultured cells, they accumulate within nuclei [Leonetti, J. P., et al., Proc. Natl. Acad. Sci. USA 88:2702 (1991)], suggesting that they may also function by interfering with transcription through formation of a third DNA strand, associated by Hoogsteen base pairing with the major groove of the B-form DNA duplex [Moffat, Science 252:1374 (1991)]. In vitro transcriptional arrest of c-myc expression was shown to operate by this mechanism in a cell-free system [cooney et al., Science 241: 456 (1988)]. Recent polyamide nucleic acid oligomers (with polyamide backbone replacing the deoxyribose phosphate backbone of DNA) were shown to cause displacement of their complementary strands from double stranded DNA [Nielsen et al., Science 254:1497 (1991)]. These newly designed drugs will selectively interrupt gene function without affecting the transcript products. In contrast, ribozyme sequences were shown to specifically interact with the mRNA transcripts. These are ribonucleic acid sequences, including RNase active sites flanked by antisense oligonucleotides [Haseloff and Gerlach, Nature 3:585 (1988)]. When targetted to the human immunodeficiency virus (HIV) they destroy HIV mRNA effectively [Sarver et al., Science 247:1222 (1990)]. However, oligoribonucleotides are more difficult to synthesize than oligodeoxynucleotides, particularly in chemically modified forms resistant to RNase attacks [Pieken et al., Science 253:314 (1991)].

Phosphorothioate antisense oligonucleotides do not show significant toxicity and exhibit sufficient pharmacodynamic half-lives in animals [Agrawal, s., et al., Proc. Natl. Acad. Sci. USA 88:7595 (1991)]. Antisense induced loss-of-function phenotypes related with cellular development were shown for the glial fibrillary acidic protein (GFAP), implicated in astrocyte growth within astrocyte-neuron cocultures [Winstein et al., J. Cell Biol., 112:1205 (1991)], for the myelin-associated glycoprotein in Schwann cells, responsible for formation of the compact myelin sheath formation surrounding these cell [Owens and Bunge, Neuron 7:56 (1991)], for the microtubule-associated tau proteins implicated with the polarity of hippocampal neurons and their axon formation [Caceres and Kosik, Nature 343:461 (1990) ], for the $\beta_1$-integrin, important for neuronal migration along radial glial cells, and for the establishment of tectal plate formation in chick [Galileo et al., J. Cel. Biol. 112:1285 (1991)] and for the N-myc protein, responsible for the maintenance of cellular heterogeneity in neuroectodermal cultures (ephithelial vs. neuroblastic cells, which differ in their colony forming abilities, tumorigenicity and adherence) [Rosolen et al., Cancer Res. 50:6316 (1990); Whitesell et al., Mol. Cell. Biol 11:1360 (1991)]. Antisense oligonucleotide inhibition of basic fibroblast growth factor (bFgF), having mitogenic and angiogenic properties, suppressed 80% of growth in glioma cells [Morrison, J. Biol. Chem. 266:728 (1991)] in a saturable and specific manner. The antisense oligonucleotides were targetted against the initiation and splice sites in bFgFmRNA, they reduced activity of the resulting protein and sense oligomers remained inactive. In soft-agar cultures, antisense oligonucleotides reduced the size of glial colonies and induced appearance of larger cells within them [R. Morrison, Neuroscience Facts 3: 3 (1992): bFGF expression in human glioma cells)].

Being hydrophobic, antisense oligonucleotides interact well with phospholipid membranes [Akhtar, S., et al., Nuc. Res. 19:5551–5559 (1991)]. Following their interaction with the cellular plasma membrane, they are actively transported into living cells (Loke, S. L., et al., Proc. Natl. Acad. Sci. USA 86:3474 (1989)], in a saturable mechanism predicted to involve specific receptors [Yakubov, L. A., et al., Proc. Natl. Acad. Sci. USA 86:6454 (1989)].

Antisense inhibition of key molecules involved in signal transduction processes may De expected to interfere also with secondary mechanisms depending on the targetted key molecule. Thus, cholinergic signaling through the $m_2$ muscarinic acetylcholine receptor is coupled to pertussis toxin-sensitive G proteins and adenylyl cyclase activity. The gamma-aminobutyric type B receptor ($GABA_B$) is similarly coupled to this signal transduction process, and both receptors are expressed in cerebellar granular neurons. Antisense oligonucleotides to the $m_2$ receptor mRNA blocked completely the synthesis of this receptor within 3 days, and reduced the $GABA_B$ receptor by 40% within 6 days. It remains to be shown whether this latter effect was due to the conserved oligo sequence being present also in the yet uncloned $GABA_B$ receptor, or whether the delay effect was secondary to $m_2$ inhibition [Morrison R., ibid.].

In view of the above-mentioned implication of cholinergic signals in the commitment and development of haematopoietic cells, it is an object of the present invention to provide for compounds and methods capable of diverting the process of cholinergic signalling, which may direct bone marrow stem cells into continued replication and re-orient their subsequent differentiation, both in culture and in vivo, into mononuclear cells of the hemopoietic and immune system.

Thus, the ChEs related antisense oligodeoxynucleotides of the present invention appear to be potent candidates for the modulation of bone marrow cells development described above. This adds to the effects of already characterized growth factors, such as the granulocyte colony stimulating factor (G-CSF), interleukin 3, 6 and 11, Lif (leukemia inducing factor) and the recently described stem cell factor, which interacts with the receptor produced from the C-kit protoncogene.

SUMMARY OF THE INVENTION

The invention relates to synthetic phosphorothioated or partially phosphorothioated oligodeoxynucleotides capable of selectively modulating hemopoietic bone marrow cells development. The term modulating as used herein refers to selective inhibition and/or stimulation of megakaryocytopoiesis and/or erythropoiesis in bone marrow cells and additionally to selective diversion of hemopoietic bone marrow stem cells development from megakaryocytes and/or erythrocytes to macrophages and mononuclear cells.

More particularly, the invention relates to synthetic phosphorothioated or partially phosphorothioated oligodeoxynucleotides capable of inhibiting or stimulating megakaryocytopoiesis and/or erythropoiesis and of diverting hemopoietic bone marrow stem cells development from megakaryocytes and erythrocytes to macrophages and other mononuclear hemopoietic cells.

The oligodeoxynucleotides of the invention are capable of modulating hemopoietic bone marrow stem cells development in vitro. Such cells can be cells extracted from patients in need of transplantation. The oligodeoxynucleotides of the invention can effectively influence the cell composition of the culture until the desired cell composition is reached, and/or can increase the number of viable stem cells in the culture.

The oligodeoxynucleotides of the invention can also modulate cell division properties in organs or tissues to be transplanted, in order to improve the procedure and decrease tissue rejection following the transplantation procedure.

The oligodeoxynucleotides of the invention can also be administered to potential donors of bone marrow or organs, prior to the donation procedure, in order to enrich the hemopoietic bone marrow fraction of specific stem cells of the hemopoiectic system.

The oligodeoxynucleotides of the invention can also be applied to embryonic or fetal bone marrow cells, prior to their storage in cell banks in order to retain such cells in viable forms devoid of tissue compatibility antigens.

Furthermore, the oligodeoxynucleotides of the invention can also be effective in the treatment of patients with certain malignant tumors, for selectively arresting the rapid cell division characteristic of the tumor tissue, while not interfering with the benign process of cell division within cells surrounding the tumor.

In particular, the invention relates to synthetic oligodeoxynucleotides being antisense oligodeoxynucleotides directed against a region spanning the AUG initiation codon in human ACHE (acetylcholinesterase) or 2HS (cdc2 kinase) genes, having phosphorothioate internucleotidic bonds between all of the nucleotides or between only the four 3'-terminus nucleotides and to synthetic oligodeoxynucleotides according being antisense oligodeoxynucleotides directed against the region spanning the AUG initiation codon in human BCHE (butyrylcholinesterase) gene or a 5'-region in the CHED (cdc2 homolog) gene, having phosphorothioate internucleotidic bonds between the four 3'-terminus nucleotides.

Still more particularly the invention relates to a synthetic antisense oligodeoxynucleotide directed against a region spanning the initiator AUG codon in the human 2HS gene having the formula: (SEQ ID NO:1)

5'-GGTATAATCTTCCAT-3' having phosphorothioate internucleotidic bonds between all the nucleotides (AS 2HS-$T_S$) or between the four 3'-terminus nucleotides (AS 2HS-$S_3$);

to a synthetic antisense oligodeoxynucleotide directed against a region spanning the initiator AUG codon in the human ACHE gene SEQ ID NOS: 5–7 having the formula: (SEQ ID NO:2)

5'-CTGCGGGGGCCTCAT-3' having phosphorothioate internucleotidic bonds between all the nucleotides (AS ACHE-$T_S$) or between the four 3'-terminus nucleotides (AS ACHE-$S_3$);

to a synthetic antisense oligodeoxynucleotide directed against a region spanning the initiator AUG codon in the human BCHE gene SEQ ID NOS: 8–9 having the formula: (SEQ ID NO:3)

5'-GACTTTGCTATGCAT-3' having phosphorothioate internucleotidic bonds between the four 3'-terminus nucleotides (AS BCHE-$S_3$); and to a synthetic antisense oligodeoxynucleotide directed against a 5'-region in the human CHED gene having the formula: (SEQ ID NO:4)

5'-TTTTCCCCAGTCAAT-3' having phosphorothioate internucleotidic bonds between the four 3'-terminus nucleotides (AS CHED-$S_3$).

The invention also relates to pharmaceutical or medical compositions comprising as active ingredient at least one of the oligonucleotides of the invention, in a physiologically or medically acceptable carrier, optionally also comprising additional physiologically acceptable additives. The active ingredient may consist of one of the oligodeoxynucleotides or of mixture/s thereof.

More particularly the compositions of the invention may be suitable for the modulation of hemopoietic bone marrow stem cells development. These compositions may inhibit abnormal hemopoietic cells proliferation. Also, the compositions may be used to enhance macrophage production and increase stem cell counts.

still more particularly the compositions of the inventions may be suitable for in vitro modulating cell division properties in organs or tissues to be transplanted in order to decrease immune response and resulting tissue rejection following the transplantation procedure. The compositions may also be used for in vitro increasing stem cell fraction in bone marrow cells to be transplanted.

Furthermore, the compositions of the invention may be used for treating embryonic or fetal bone marrow cells prior to their storage in cell banks in viable forms devoid of tissue compatibility antigens, comprising as active ingredient the oligodeoxynucleotides of the invention, in a pharmaceutically acceptable carrier, optionally also comprising additional physiologically acceptable agents. The active ingredient may consist of one of the oligodeoxynucleotides or of mixture/s thereof.

Additionally, the compositions of the invention may be used for treatment of organ donor and recipient, prior to the donation procedure, to decrease the immune response in procedures of allotransplantation, and for the treatment of potential bone marrow donors, prior to the extraction of the bone marrow, in order to enrich the hemopoietic bone marrow fraction of specific stem cells of the hemopoietic system.

Still further, the compositions of the invention may be used for treating patients with malignant tumors, selectively arresting cell division in the tumor tissue, but not in the benign cells surrounding the tumor. These compositions may be particularly suitable for the treatment of chondrosarcomas.

The invention also relates to methods of modulating hemopoietic bone marrow stem cells development in patients in need of such treatment by administering to the patient a therapeutically effective amount of the oligodeoxynucleotides or compositions of the present invention. For example, abnormal hemopoietic cells proliferation may be inhibited, macrophage production enhanced and stem cell counts increased by the methods of the present invention.

The invention also relates to methods of in vitro modulating cell division properties in organs or tissues to be transplanted, in order to decrease immune response and resulting tissue rejection following the transplantation procedure, by contacting the organ with an effective amount of the oligodeoxynucleotides or compositions of the invention under conditions suitable culture conditions appropriate for allotransplatations procedures. These methods may also be used for in vitro increasing stem cell fraction in bone marrow cells samples to be transplanted.

Furthermore, the invention also relates to methods of treating embryonic or fetal bone marrow cells prior to their storage in cell banks in viable forms devoid of tissue compatibility antigens, by contacting a sample with the oligodeoxynucleotides or compositions of the invention under suitable culture conditions.

Additionally, the methods of the invention encompass treatment of organ donor and recipient, prior to the donation procedure, to decrease the immune response in procedures of allotransplantation, and of potential bone marrow donors, prior to the extraction of the bone marrow, in order to enrich the hemopoietic bone marrow fraction of specific stem cells of the hemopoietic system.

Still further, the invention relates to methods of treating patients with malignant tumors, selectively arresting cell division in the tumor tissue, but not in the benign cells surrounding the tumor by administering to the patient in need of such treatment a therapeutically effective amount of the oligodeoxynucleotides or compositions of the invention. These methods may be particularly suitable for the treatment of chondrosarcomas.

[$^{35}$S]-labeled RNA transcripts composed of the "sense" (mRNA) or "antisense" (cRNA) strands complementary to the cDNAs encoding AChE and BuChE were prepared as detailed under Material and Methods (4) from the pGEM-7Z(+) and Bluescript SK(+) plasmids, using T7, SP6 or T3 RNA polymerases. Informative restriction sites are noted for the cDNA inserts and their boundary polylinker domains. The labeled RNA products were further subjected to controlled alkaline hydrolysis to produce sufficiently shortened probes for in situ hybridization.

Figure 2A:
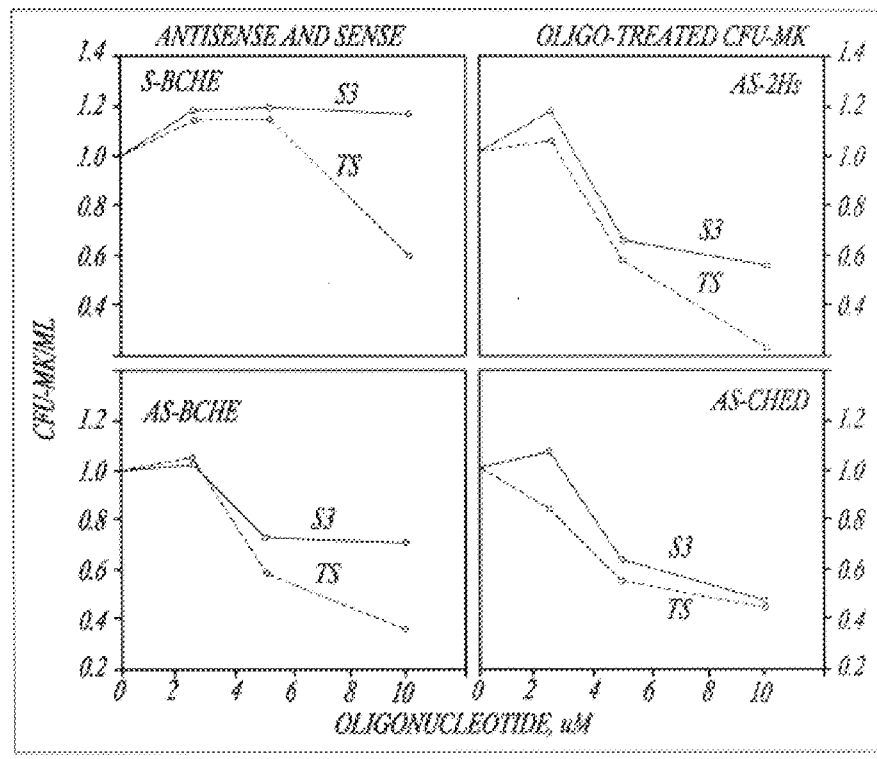

FIG. 2A Titration curves of IL$_3$-treated murine bone marrow cells cultures with $S_3$ or $T_S$ oligodeoxynucleotides (Antisense—AS; Sense—S).

Bone marrow cells were grown in methyl cellulose/LPM (Beit Haemek), 1% BSA (Sigma) and 10% WEHI-CM, a source of IL-3. They were incubated at 37° C. and 5% $CO_2$ at a cell concentration of $10^5$ cells/ml. AS- and S-oligodeoxynucleotides were prepared at stock concentrations of 2–4 mM made in 10 mM Tris +1 mM EDTA, pH 7.5, and were kept frozen at −20° C. until use. They were subsequently diluted in PBS to 100 $\mu$M and added to cultures at time 0 to give final concentrations of 2.5–10 $\mu$M. The oligodeoxynucleotides were retained in the culture throughout the experiment. Colonies were scored on Day 4 with a Zeiss stereozoom microscope equipped with an optic fiber dark field device.

Figure 2B:
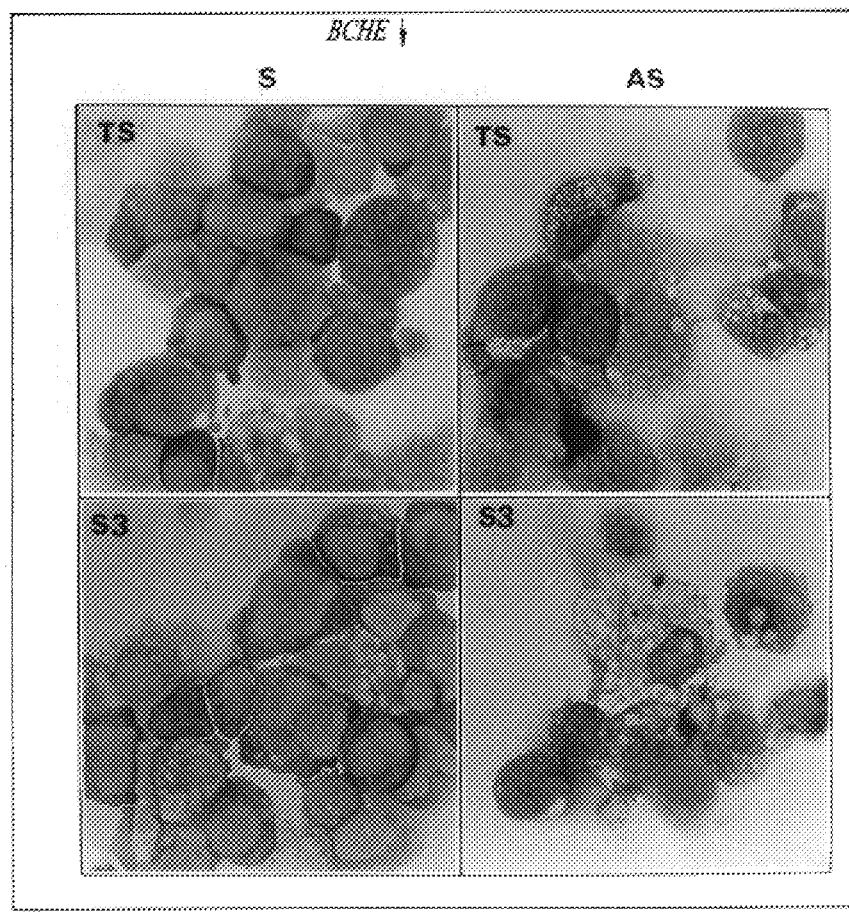

FIG. 2B Representative fields for cultured bone marrow cells treated with sense and antisense BCHE oligodeoxynucleotides of the $T_S$ and $S_3$ types at 5 $\mu$M concentrations and 4 days incubation.

Figure 3:
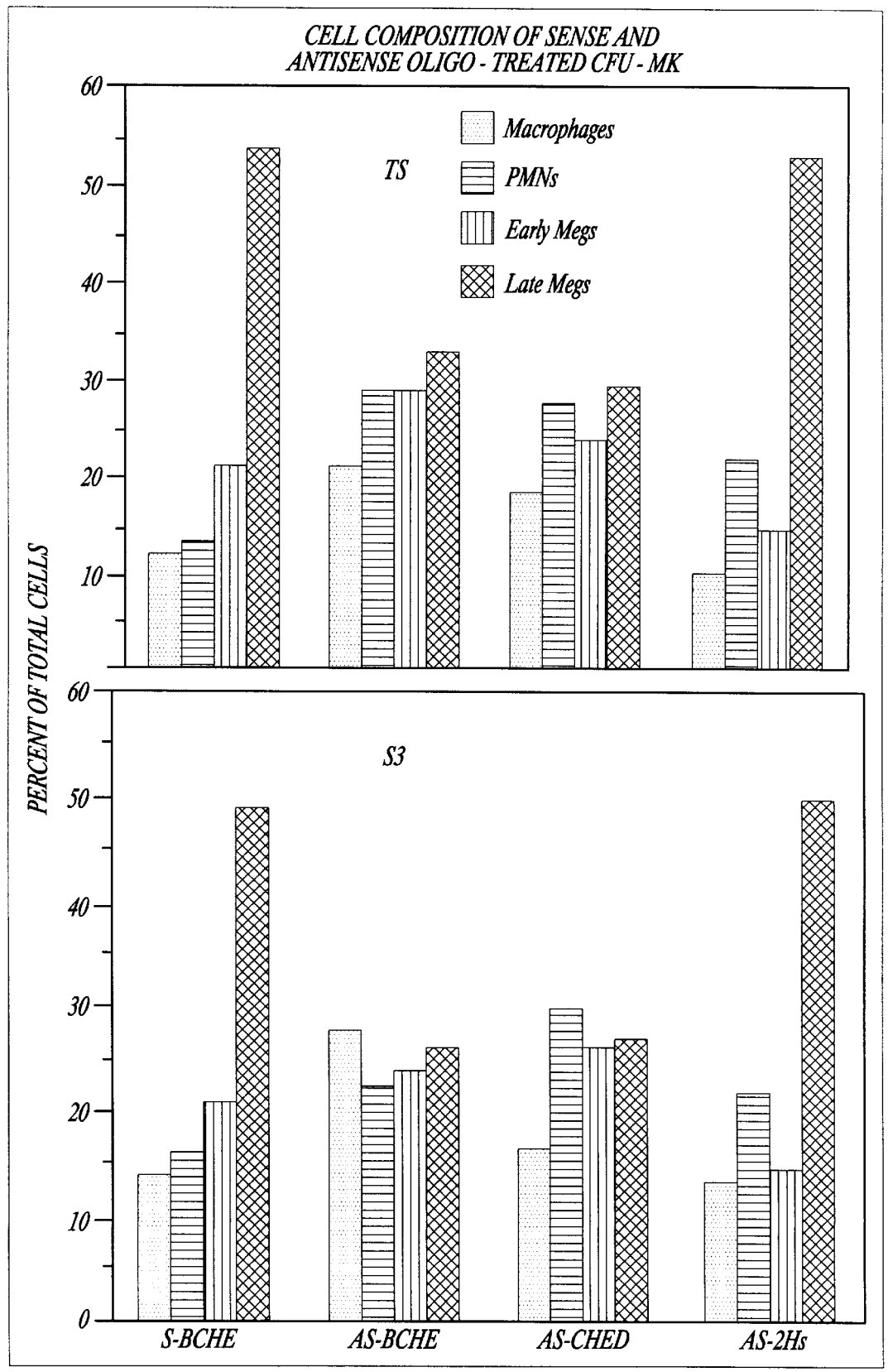

FIG. 3 Cell composition of sense and antisense oligodeoxynucleotides-treated megakaryocyte colonies, grown in the presence of IL3 only (megakaryocytopoietic conditions).

Total contents of plates were scraped and collected on Day 4, washed once with PBS and cytocentrifuged. Cells were stained with May-Grunwald Giemsa and at least 1,000 cells counted per given experimental condition. Cells were classified according to the same criteria as in Patinkin et al., Mol. Cell Biol., 10:6046, (1990).

FIG. 4 The Table presents data of several molecular parameters of the various oligodeoxynucleotides and their variable effects in inhibiting colony formation under megakaryocytopoietic conditions.

Figure 5:
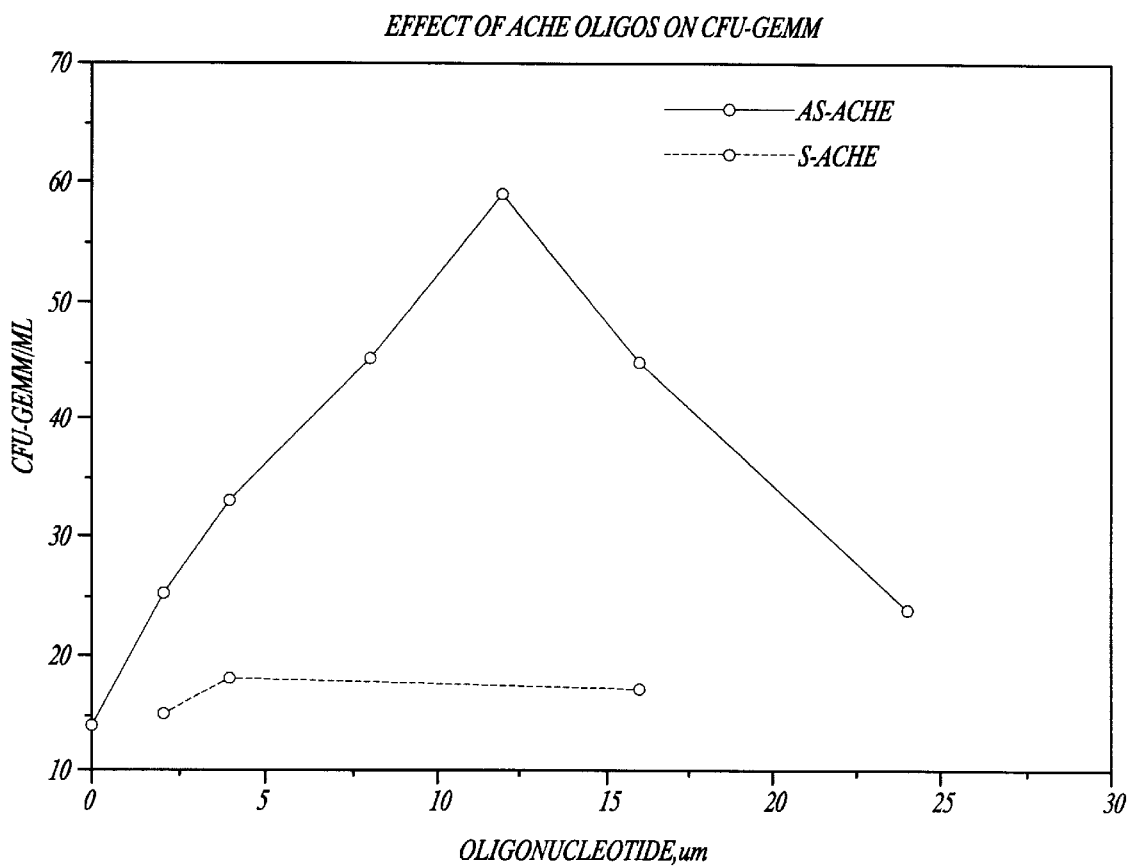

FIG. 5 Titration curves of colony formation following administration of oligodeoxynucleotides under erythropoietic conditions, with also transferrin and erythropoietin (EPO) added (CFU-GEMM).

For the CFU-GEMM conditions bone marrow cells were grown in methyl cellulose/LPM (Beit Haemek) containing $10^{-4}$M thioglycerol (Sigma), 1% BSA (Sigma), 10% WEHI-CM (containing IL-3), $2.8 \times 10^{-4}$M iron-saturated human transferrin (Behring, Marburg) and 2 units erythropoietin (EPO, 1,000u/mg)(Terry Fox Labs, Vancouver, B.C). Colonies were scored after 8 days incubation at 37° C. and 5% $CO_2$, using a Zeiss stereozoom micro scope equipped with an optic fiber dark field device.

Figure 1:
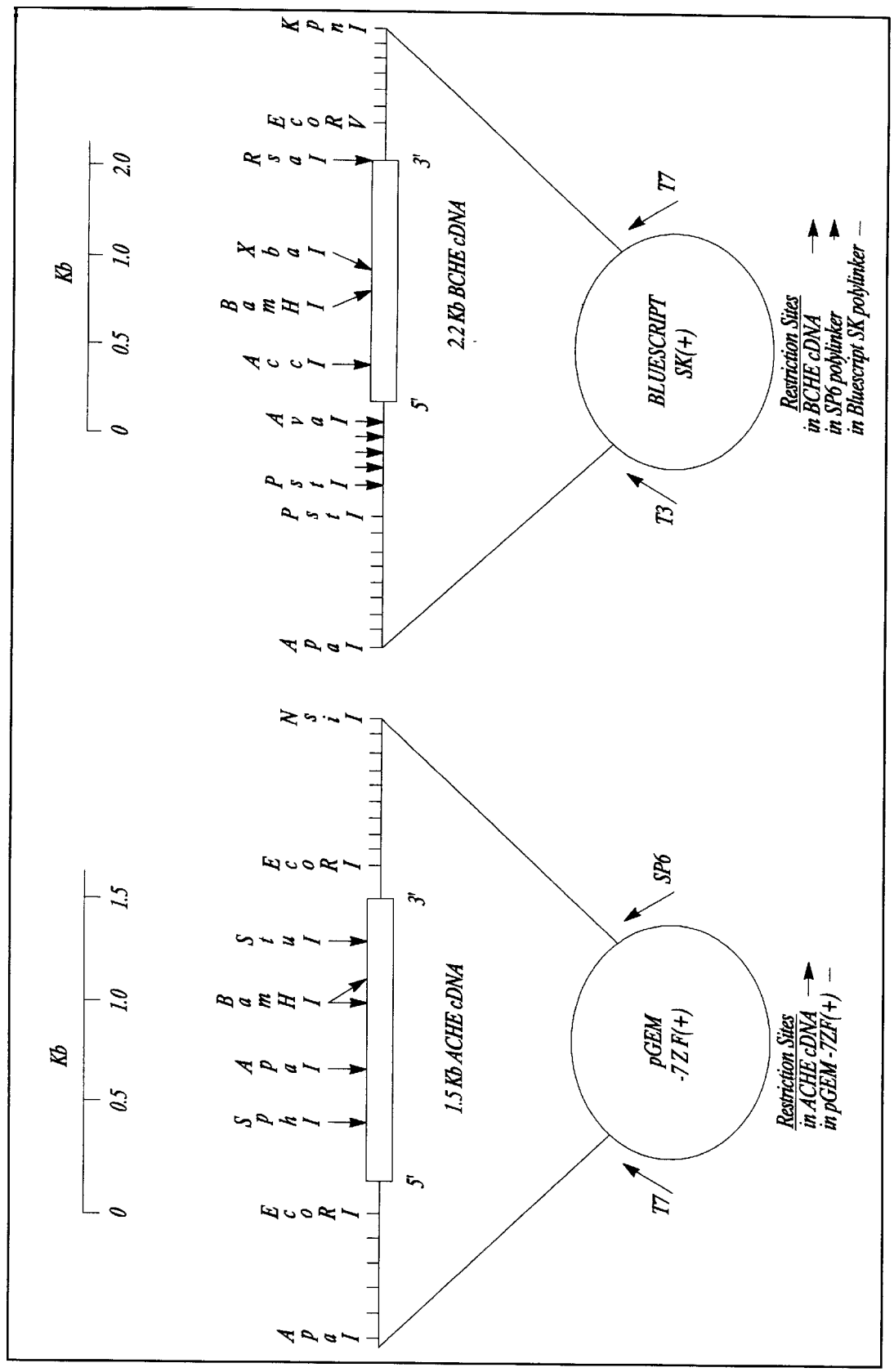
FIG. 1 Transcription vectors for ChERNAs.
Figures 1, 6A:
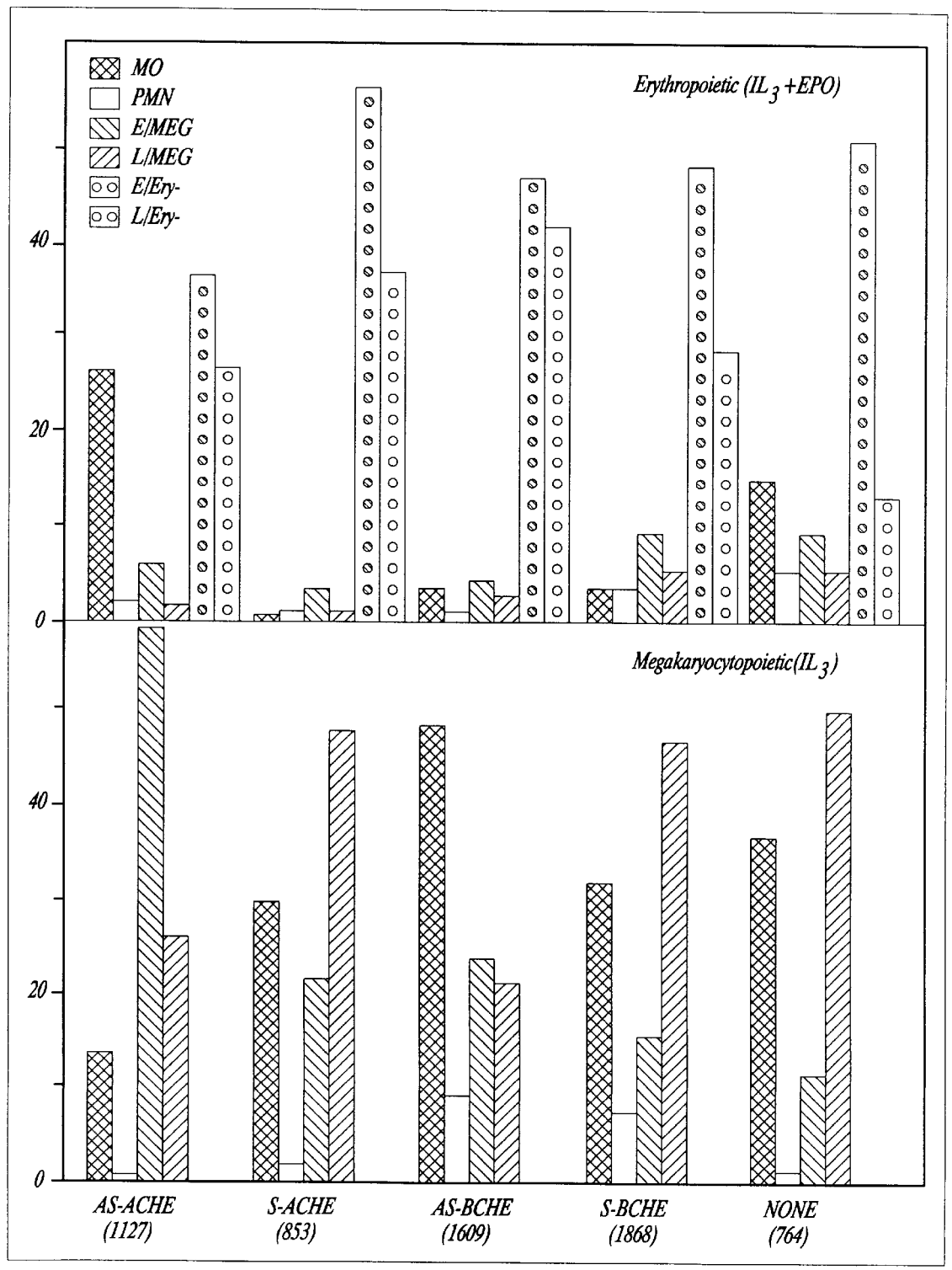
Figures 2, 6A:
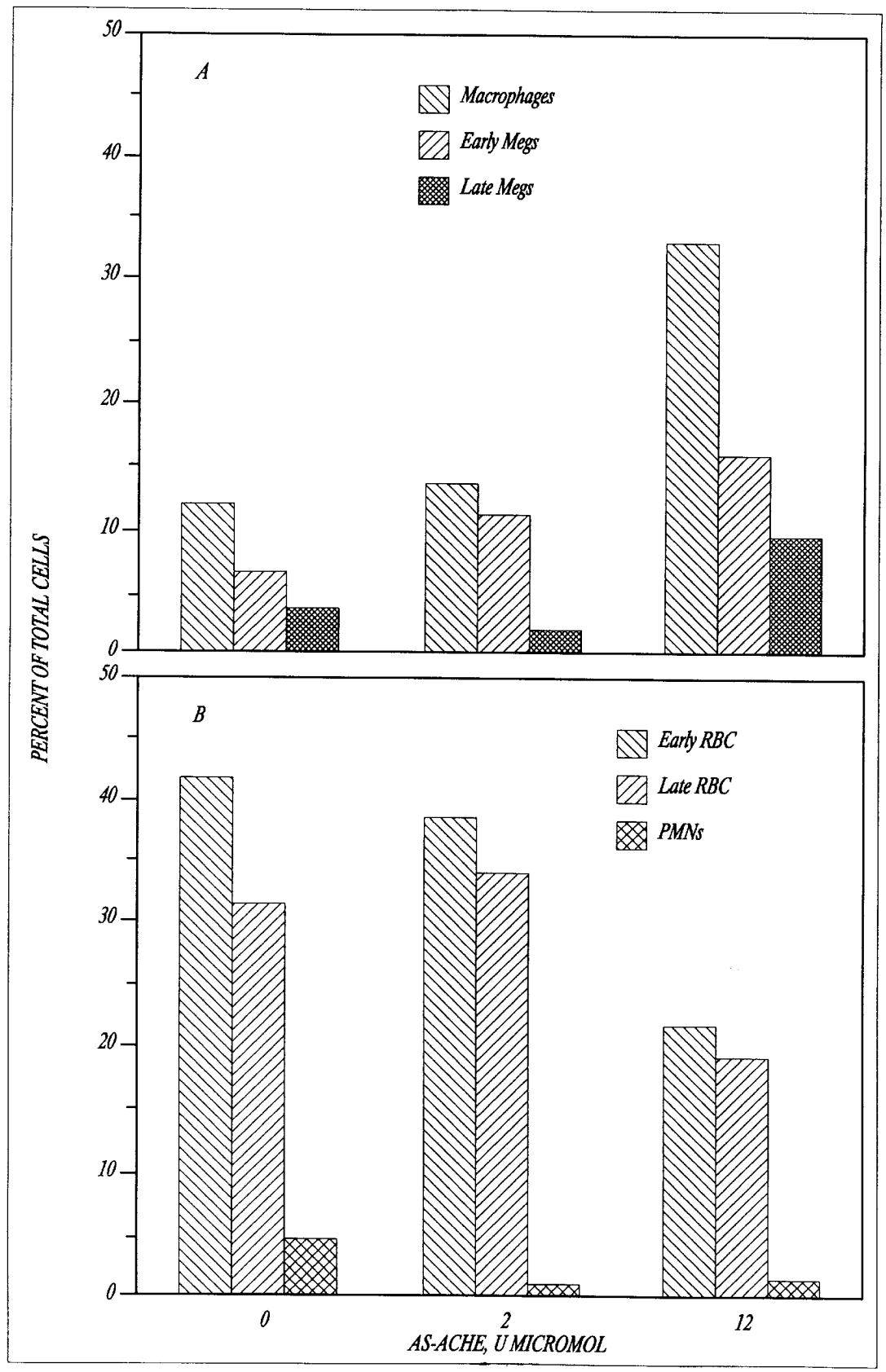

FIG. 6A1–2: 6A1 Differential cell counts of hematopoietic cells grown in culture in the presence of oligodeoxynucleotides. Mouse primary bone marrow cells were grown in culture as in Patinkin et al., 1990 in the presence of 2 μM AS-ACHE or S-ACHE oligomers or of 4 μM AS-BCHE or S-BCHE oligomers. Growth conditions were in the presence of interleukin 3 and erythropoietin (top panel) or interleukin 3 alone (bottom panel). Columns present percent fractions of macrophages (MØ), polymorphonuclear cells (PMN), early and late megakaryocytes (E,L/MEG) and early and late erythroid cells (E,L/Ery) (upper left corner key).

6A2 Dose-dependent changes in the differential subclasses of cultured hematopoietic cells subjected to AS-ACHE treatment. Presented are cell types the fractions of which increase under AS-ACHE treatment in a dose-dependent manner (macrophages, early and late megakaryocytes, top A panel) and those cell types the fractions of which decrease under such treatment (early and late red blood cells, RBC, and polymorphonuclear cells, PMNs, bottom B panel).

Figure 7:
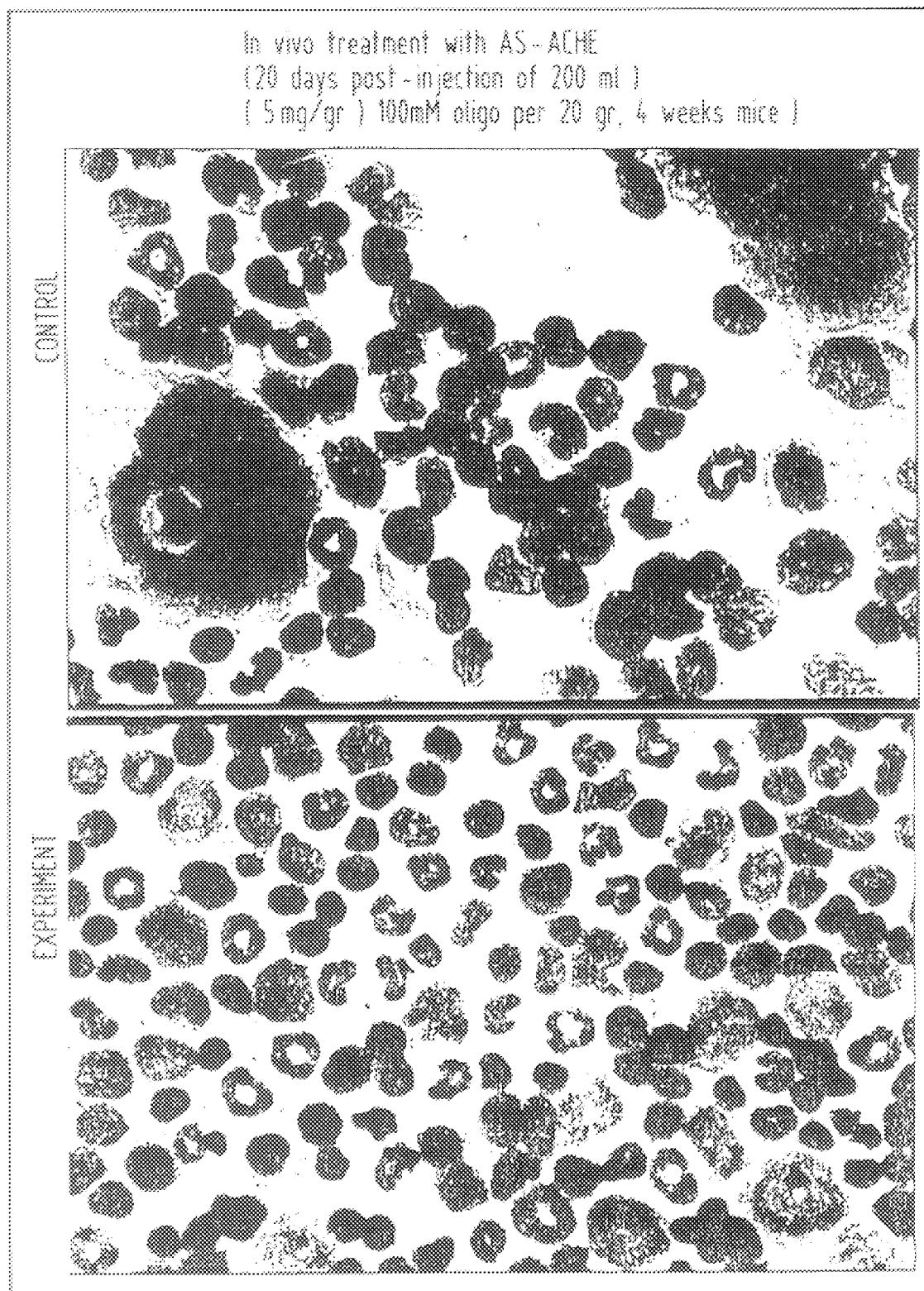

FIG. 7 Representative micrographs of bone marrow smears of mice injected once, intraperitoneally, with 25 μg/g body weight AS-ACHE, 20 days post-injection or with phosphate buffered saline (PBS) for control.

Figure 8:
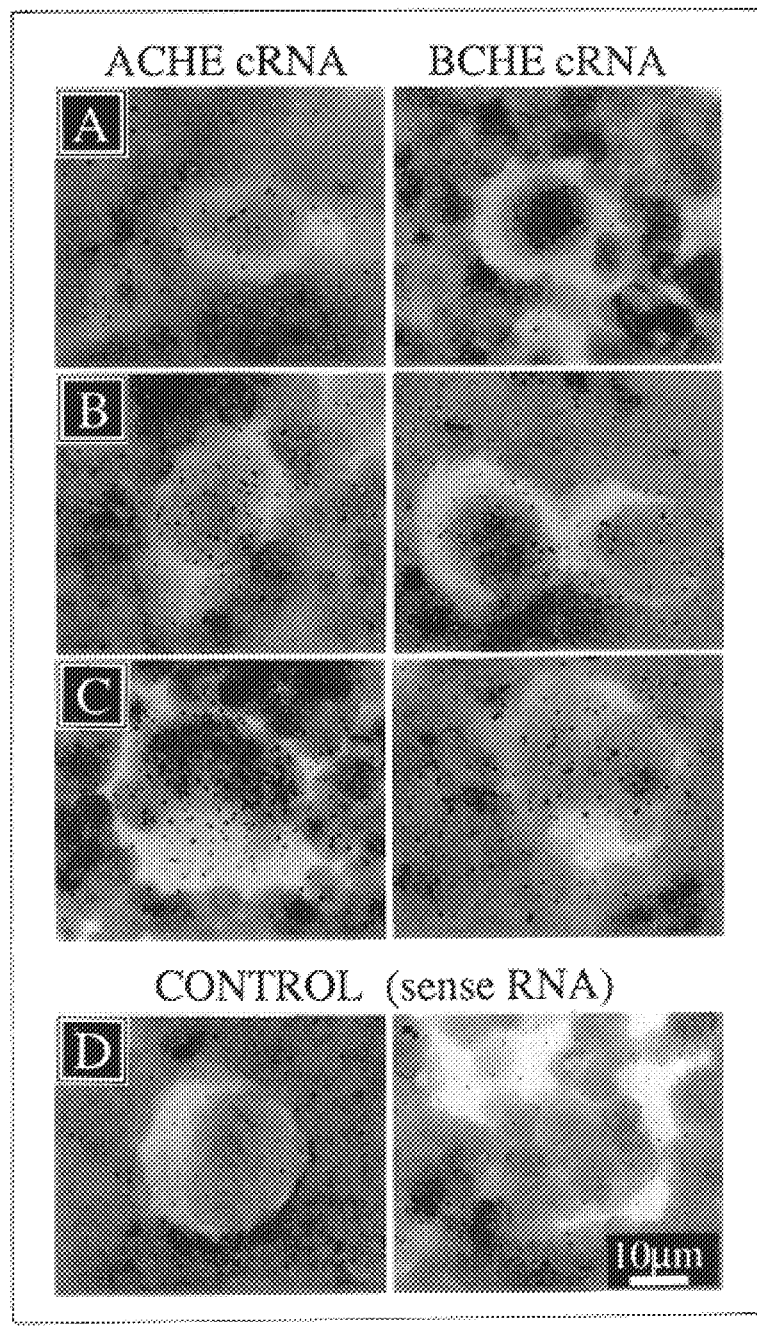

FIG. 8 ChEcRNA labelings increase with megakaryocytes development.

Bone marrow smears from untreated female mice were subjected to in situ hybridization with the noted [$^{35}$S]-labeled ChERNA probes. Labeled megakaryocytes (MK) were photographed following emulsion autoradiography as detailed under Methods.

A: Promegakaryocytes;

B: Intermediary cells;

C: Mature, polynuclear megakaryocytes.

Note the increase in grain no./cell which accompanies megakaryocytes development, the difference between AChEmRNA and BuChEmRNA labelings and the absence of grains over cells hybridized with the control ("sense") probes.

Figure 9:
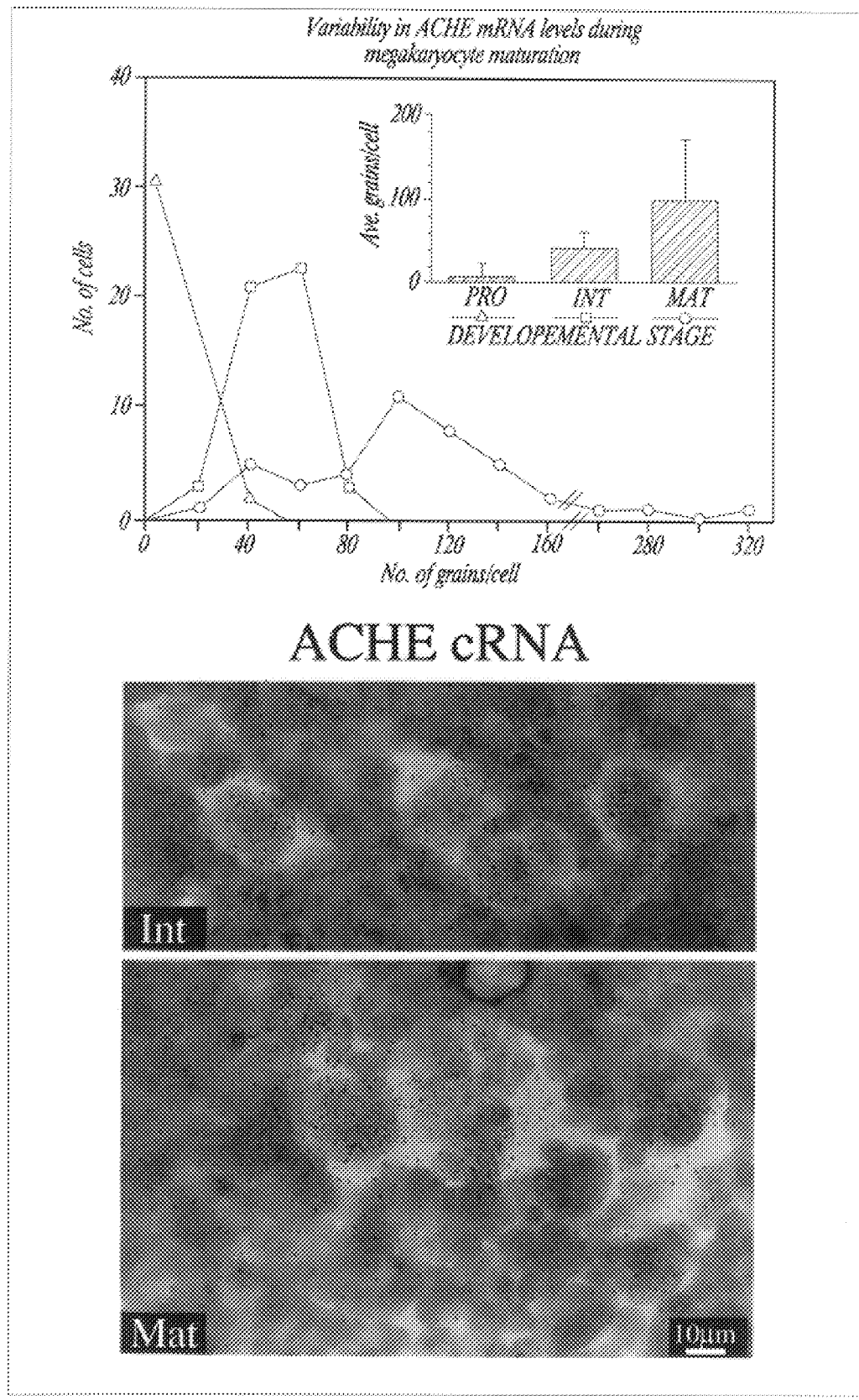

FIG. 9 Variability in AChEmRNA levels during megakaryocyte maturation.

A: The average no. of grains per cell was determined for the noted no. of megakaryocytes at the pro (—▲—), intermediary (—□—) and mature (—●—) stage. Cells were divided to groups according to their developmental stage and the no. of grains over them (from 0 to 20, from 20 to 40 etc.,). Curves represent the distribution of grain density for each of the megakaryocyte subtypes. Note the wider variability of grains over mature as compared with intermediary and promegakaryocytes and the larger no. of intermediary cells as compared with the other groups.

Inset: Average no. of grains per cell type is shown in a histogram. Background labeling over slide areas uncovered by cells, representing spontaneous grain formation in the photographic emulsion did not exceed 5% of the signal and was subtracted from the experimental results.

B: Variable labeling over intermediary and mature megakaryocytes is shown in emulsion autoradiography micrographs. Note that various nuclei and cells are labeled with different intensities. The empty space around nuclear clusters is probably due to receding cytoplasm at the preparation steps prior to the in situ hybridization procedure [Courtney, M., et al., Blood 77:560–568 (1991)].

Figure 10:
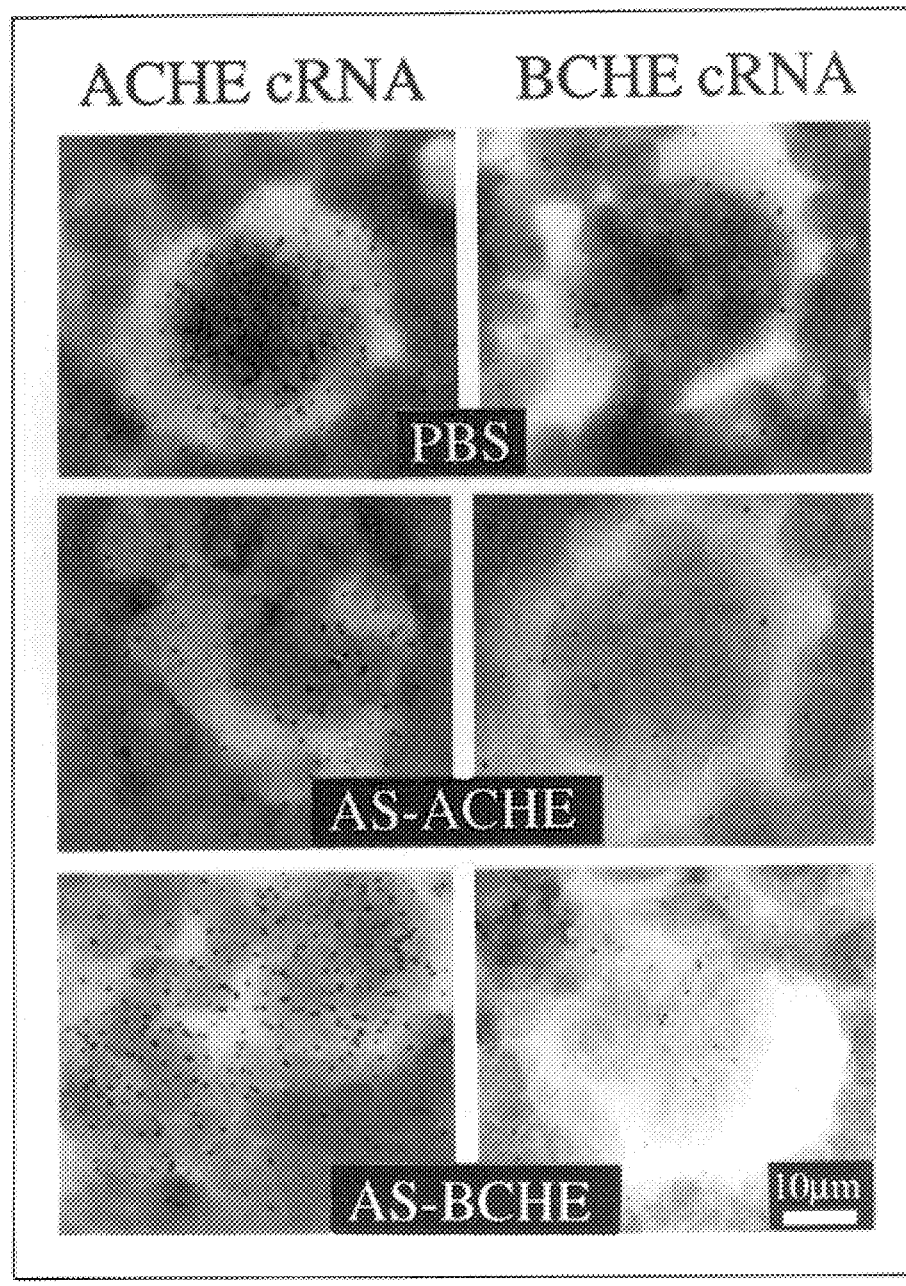

FIG. 10 Labeling variations in mice administered in vivo with AS-CHE oligodeoxynucleotides.

Bone marrow smears were prepared from adult female mice treated once with "antisense" phosphorothiothioate oligodeoxynucleotides or with PBS as detailed under methods, 3 weeks after the treatment. In situ hybridization and emulsion autoradiography were performed in parallel. The presented photographs display smears hybridized with antisense AChEcRNA or BChEcRNA from a single mouse out of each treatment group. Note the lower intensity labeling with BuChEcRNA as compared with AChEcRNA in all mice, and the reduction in labeling intensity in the treated as compared with PBS injected mice.

Figure 11:
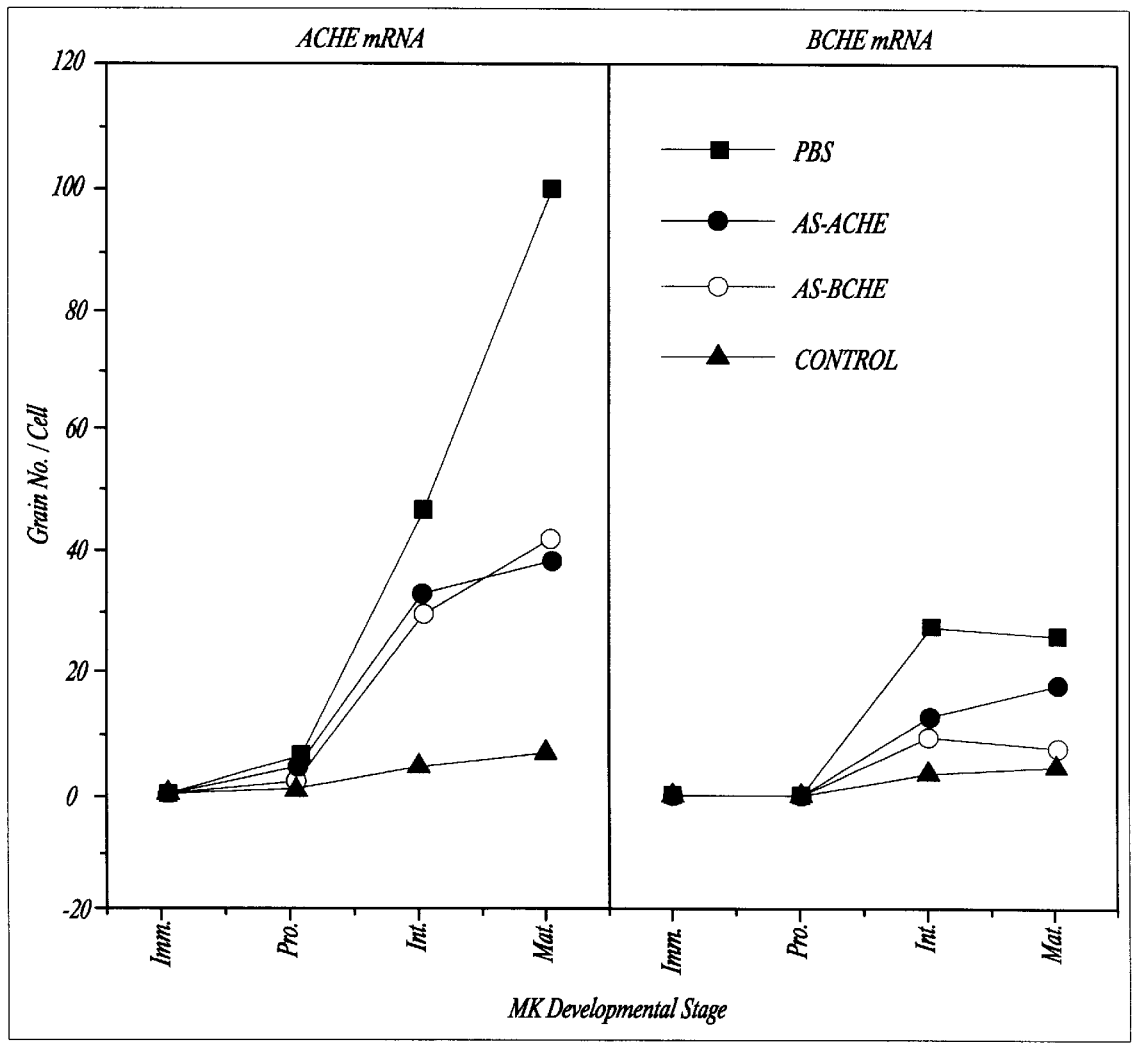

FIG. 11 Modulation of ChEmRNA levels in megakaryocytes from control and AS-CHE treated mice.

ChEmRNA levels in immature, pro-, intermediary and mature megakaryocytes were determined in average no. of grains per cell as detailed in text for mice treated with PBS, AS-ACHE and AS-BCHE. "Sense" AChEmRNA and BuChEmRNA probes served for controls and bone marrow smears hybridized with them remained practically unlabeled (see empty symbols in top drawing). Note differences in the developmental patterns of labeling with the two cRNA probes and reductions in these labelings in mice treated with AS-CHEs.

FIG. 12 Cell count alterations in megakaryocyte populations from AS-ACHE and AS-BCHE treated mice.

Total counts of megakaryocytes for each bone marrow smear were averaged within each treatment group (N=4) and are shown with their standard deviations. Columns represent average % fractions of specific megakaryocyte subtypes within these groups. Deviations are marked at column tops. Note variations in total megakaryocyte number and altered differential cell counts for AS-ACHE, but not AS-BCHE treated mice as compared with the PBS-injected controls.

Figure 13A:
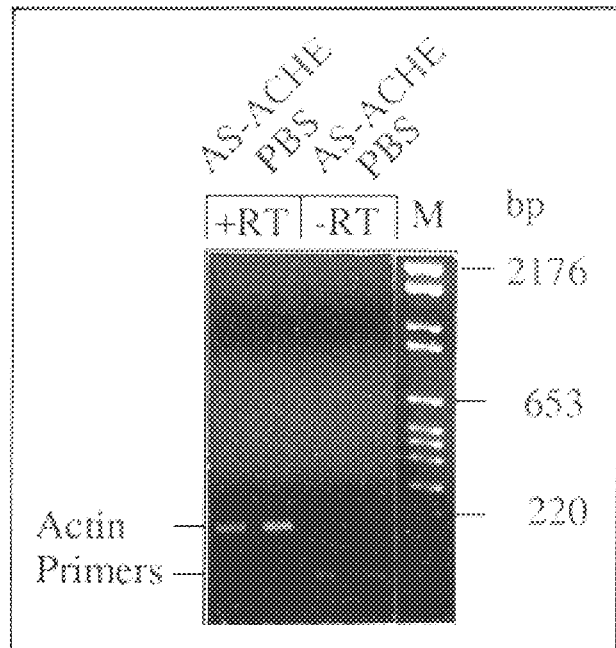
Figure 13B:
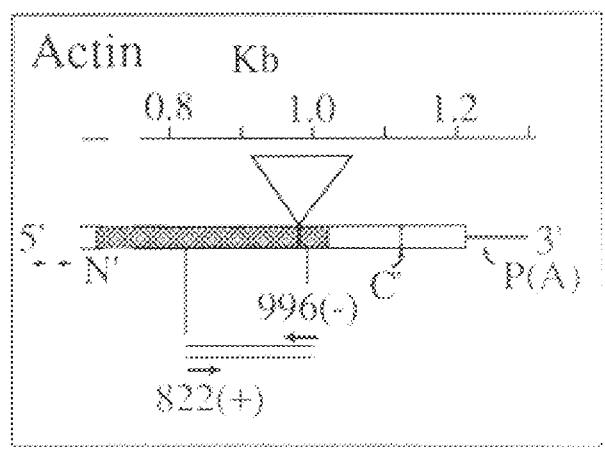

FIG. 13 Suppression of ChEmRNA levels is selective as observed by normal levels of actin mRNA transcription in AS-ACHE-treated mice.

13A: Selective PCR amplification of β-actine mRNA from AS-ACHE-treated and untreated (PBS) mice.

Total RNA was extracted from bone marrow of AS-ACHE phosphorothioate oligodeoxynucleotide or PBS injected mice using the RNasol method according to manufacturer's instructions. 1 μg RNA was reverse transcribed using random hexamers as primers. The resultant cDNA was PCR amplified with the mouse β-actine specific primers 822(+) and 996(−) [Lapidot-Lifson, Y., et al., Proc. Natl. Acad. Sci. USA 89: 579–583 (1992)] using the RNA-PCR kit (Perkin Elmer/Cetus), according to manufacturer's instructions. PCR conditions were: denaturation: 94° C., 1 min. (1st cycle 3 min.); annealing: 55° C., 1 min.; elongation: 72° C., 1 min. (last cycle 5 min.), 35 cycles. PCR products (10%) were analyzed on ethidium bromide stained 1.6% agarose gel. Note the presence of β-actin PCR fragment (175 bp) in apparently similar amounts in AS- ACHE and PBS injected mice in the presence of reverse transcriptase (+RT) and its absence where reverse transcriptase was not included in the reaction mixture (−RT), M, molecular weight marker (marker VI, Boehringer Mannhiem); bp, base pairs.

13B: Schematic presentation of the mouse actin gene. Positions of the 822(+) and 966(−) primers within the coding region of actin cDNA as related to the exon/intron structure of the mouse β-actine gene is shown. N' and C' denote the amino and carboxyl termini of the mature protein. P(A), the polyadenylation signal; a ▽ denotes the position of intron. The length is shown in kb.

Figure 14:
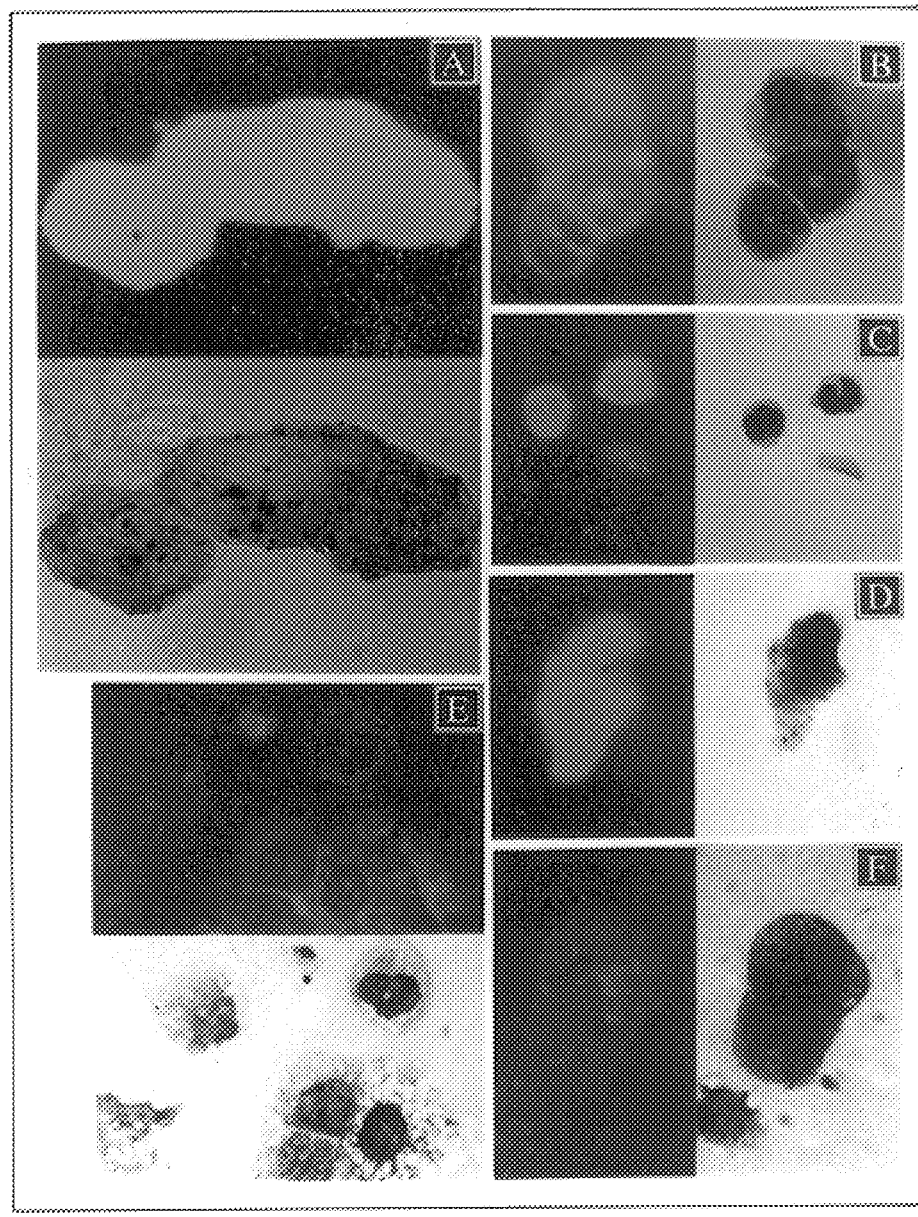

FIG. 14 Cytoplasmic accumulation of AS-oligodeoxynucleotides.

AS-CHED covalently bound to a fluorescent FITC tag was administered at final concentration of 4 μM to CFU-MEG cultures. 2 hr. and 4 days after, cells were cytospinned and stained as detailed under Methods. Fluorescent photography using a Zeiss Axioplan microscope and a ×100 Plan neofluar lense was then employed to reveal subcellular localization (S) of the AS-oligodeoxynucleotide within treated cells. Analyzed cell types included mature megakaryocytes (A), mixed colonies containing young, dividing megakaryocytes and mature polymorphonuclear cells (B), and yet smaller polymorphonuclear cells, early in their development (C).

DETAILED DESCRIPTION OF THE INVENTION

The invention relates to synthetic phosphorothioated or partially phosphorothioated oligodeoxynucleotides capable of selectively modulating hemopoietic bone marrow cells development.

More particularly the invention relates to synthetic phosphorothioated or partially phosphorothioated oligodeoxynucleotides capable of inhibiting or stimulating megakaryocytopoiesis and of diverting hemopoietic bone marrow stem cells development from megakaryocytes and erythrocytes to dividing stem cells, macrophages and other mononuclear cells.

In particular, the invention relates to synthetic oligodeoxynucleotides being antisense oligodeoxynucleotides directed against a region spanning the AUG initiation codon in human ACHE (acetylcholinesterase) or 2HS (cdc2 kinase) genes, having phosphorothioate internucleotidic bonds between all of the nucleotides or between only the four 3'-terminus nucleotides and to synthetic oligodeoxynucleotides being antisense oligodeoxynucleotides directed against a region spanning the AUG initiation codon in human BCHE (butyrylcholinesterase) or a 5'-region in CHED (cdc2 homolog) genes, having phosphorothioate internucleotidic bonds between the four 3'-terminus nucleotides.

Specific synthetic antisense oligodeoxynucleotides according to the present invention are the following:

an antisense oligodeoxynucleotide directed against a region spanning the initiator AUG codon in the human 2HS gene having the formula:

5'-GGTATAATCTTCCAT-3' (SEQ ID NO:1)

having phosphorothioate internucleotidic bonds between all nucleotides (AS 2HS-$T_S$) or between the four 3'-terminus nucleotides (AS 2HS-$S_3$);

an antisense oligodeoxynucleotide directed against a region spanning the initiator AUG codon in the human ACHE gene having the formula:

5'-CTGCGGGGGCCTCAT-3' (SEQ ID NO:2)

having phosphorothioate internucleotidic bonds between all nucleotides (AS ACHE-$T_S$) or between the four 3'-terminus nucleotides (AS ACHE-$S_3$);

an antisense oligodeoxynucleotide directed against a region spanning the initiator AUG codon in the human BCHE gene having the formula:

5'-GACTTTGCTATGCAT-3'(SEQ ID NO:3)

having phosphorothioate internucleotidic bonds between the four 3'-terminus nucleotides (AS BCHE-$S_3$); and an antisense oligodeoxynucleotide directed against a 5'-region in the human CHED gene having the formula:

5'-TTTTCCCCAGTCAAT-3' (SEQ ID NO:4)

having phosphorothioate internucleotidic bonds between the four 3'-terminus nucleotides (AS CHED-$S_3$).

The partially phosphorothioated oligodeoxynucleotides are preferred.

The phosphorothioated and partially phosphorothioated 15-mer oligodeoxynucleotides can be synthesized, for example, by using an Applied Biosystems 380B DNA synthesizer, as will be described in more detail in the following Examples.

To examine the concentration dependence of the antisense oligodeoxynucleotides and to determine their toxicity levels, titration curves were obtained for each of the present oligodeoxynucleotides, using megakaryocytopoietic bone marrow cultures. As may be seen from Experimental Example 1, both the fully ($T_S$) and partially ($S_3$) phosphorothioated oligodeoxynucleotieds AS-BCHE, AS-2HS and AS-CHED reduced colony counts specifically. However, the $S_3$ oligodeoxynucleotides were considerably less toxic than their $T_S$ equivalents. As may be seen from this Example and FIGS. 1 and 2, the fraction of megakaryocytes was significantly reduced and a matching increase in macrophages was observed for AS-BCHE and AS-CHED, but not for AS-2HS or S-BCHE treatments. Thus, the antisense BCHE and CHED oligodeoxynucleotides of the invention are capable of reducing megakaryocytopoiesis and stimulating macrophages formation.

In addition, several molecular parameters of the various oligodeoxynucleotides, such as thermodynamic properties, dimer formation, hydrogen bonds, intramolecular hybridization, as well as their potential for inhibiting colony formation were determined. Results are given in Experimental Example 2.

The effects of the present oligodeoxynucleotides in cell cultures under megakaryocytopoietic conditions, were compared with those in cell cultures under erythropoietic conditions. Remarkably, megakaryocytopoiesis was efficiently blocked by both AS-ACHE and AS-BCHE under megakaryocytopoietic conditions, while stimulation of cell proliferation was observed for AS-ACHE under erythropoietic conditions, with 10-fold increase in colony counts and an accompanying increase in megakaryocyte fractions. To the best of the inventors' knowledge, induction of cell proliferation by in vitro oligodeoxynucleotide treatment has not been demonstrated at the date of the application. Results are given in Experimental Example 3.

Furthermore, the different oligodeoxynucleotides of the invention exhibit specific effects which were examined by comparable colony counts. Treatment, in culture, with ASACHE, at low concentration (2 μM) was shown to be accompanied by a selective decrease in megakaryocytes under CFU-MEG (megakaryocytopoietic) conditions and reduction in erythrocytes under CFU-GEMM (erythropoietic) conditions. At relatively high concentrations (12 μM), treatment, in culture, with AS-ACHE further increases the number of megakaryocytes, under erythropoietic conditions, as observed in cultures. Treatment, in culture, with AS-BCHE, but not with S-BCHE, at 4 μM concentration, reduced megakaryocytopoiesis under both megakaryocytopoietic and erythropoietic conditions.

Results are given in Experimental Example 4.

Experiments in vivo show an increase in lymphocytes, including the desired stem cells, following treatment with ASACHE. The effect is specific and concentration-dependent, and was observed 3 and 6 weeks following a single injection of the AS-ACHE, but not the S-ACHE oligodeoxynucleotides. Parallel decrease in erythrocytes accompanied this drastic change in bone marrow composition. These important results are given in Experimental Examples 5 and 8.

The above effects were further substantiated by the increased ChEmRNA levels through megakaryocytes maturation in untreated mice, which were altered following treatment with the oligodeoxynucleotides of the invention. Results are given in Experimental Examples 6 and 7.

The present findings suggest that in vivo treatment with low amounts of the synthetic phosphorothioated or partially phosphorotioated antisense oligodeoxynucleotides of the present invention can modulate platelet production. The present findings demonstrate prolonged hematopoietic effects of intraperitoneally injected AS-oligodeoxynucleotides on the mRNA levels of their target sequences as well as on the composition and/or total number of megakaryocytes on the other hand. As can be seen in Table 2, the fractions of other hemopoietic bone marrow cells are also influenced by these anti-sense oligodeoxynucleotides.

The inventors have used in situ hybridization followed by image analysis and statistical management of labeling results. This high resolution approach demonstrated a 20-fold increase in AChEmRNA levels and a more modest 4-fold increase in BuChEmRNA from promegakaryocytes to mature, platelet-producing megakaryocytes. It may be noted that the enzymatic activities of AChE and BuChE are both visible at all these developmental stages, and even in the apparently unlabeled immature cells [Burstein et al., [1980); Patinkin et al., (1990)]. However, the histochemical analysis did not allow for quantification. The results presented in the following Examples therefore imply that the various CHE genes undergo a considerable transcriptional activation during the megakaryocytopoietic process.

The complex regulation of CHE genes in mammalian megakaryocytopoiesis suggests distinct roles for AChE and BuChE in the development of these cells. This notion is reinforced by the AS-CHE treatments and their effects on the number and composition of megakaryocytes in the treated mice, as shown in the Examples. Furthermore, these findings present the first steps towards the development of an in vivo paradigm for the selective inhibition of CHE genes expression using oligodeoxynucleotide-based therapeutical preparations. Finally, the present observations indicate that platelet production in vivo is controlled by cholinergic signalling. The development-suppressing effect of AS-BCHE both in $IL_3$-treated cell cultures and in vivo further suggests that erythropoietin, which was absent from the cultures, does not principally alter the effect of AS-BCHE, although the extent of suppression may not be similar in culture and in vivo.

AS-ACHE suppresses selectively its target mRNA while moderately effecting BuChEmRNA levels. In contrast, AS-BCHE decreases both ChEmRNAs, though with higher efficiency for BuChEmRNA. Previous culture studies demonstrated a general inhibition of megakaryocytopoiesis by AS-BCHE [Patinkin et al., (1990)]. However, its effect on AChEmRNA is significant: the AChEmRNA decrease may not be attributed to the general slowdown in megakaryocytopoiesis, as it appeared in cells measured precisely as belonging to specific subgroups. This, in turn, sheds more light on the variability in AChEmRNA labeling in what the inventors defined as mature megakaryocytes. Thus, cells seem to accumulate AChEmRNA molecules with aging, perhaps to ensure that nuclear division and development will cease in these cells.

It is a purpose of the invention to provide compounds and methods which would improve treatment protocols for blood and immune system diseases. Increasing the fraction of stem cells in bone marrow to be transplanted may shorten the delay period through which the transplanted bone marrow does not yet proliferate efficiently enough and the recipient is in need of receiving fresh blood transfusions. Treating the recipient's own prefrozen bone marrow (for example bone marrow may be extracted from patients before commencing chemotherapy or radiotherapy) with the oligodeoxynucleotides of the invention will avoid the current need for immune suppression following the transplantation procedure.

According to current procedures, $2 \times 10^8$ bone marrow cells per kg body weight are needed for transplantation. A single extraction involves 10–15 ml bone marrow tissue. Increasing the number of proliferating stem cells in such samples will improve the results of the transplantation. Furthermore, small seed samples can thus be grown into sizable cell populations. This can assist in storing a prospective recipient's own cells since such seed cultures may be prepared, for example from the umbilical cord and can be kept frozen, HLA typed, until needed.

In addition, the antisense-oligodeoxynucleotides of the present invention are potentially important for use in immunosuppression procedures. Modification of immune function by pharmacological agents is emerging as a major area of therapeutics, particularly in clinical procedures required for allotransplantation. Activation or suppression of the immune response are both believed to involve processing of the "self" or "non-self" antigens by phagocytic cells such as macrophages [for a comprehensive review of this topic see Paul, W. E., Fundamental Immunology, 2nd Ed., Raven Press, N.Y. 1989]. Therefore, rationalized modulation of hemocytopoiesis should be of value for transplantation procedures. Thus, suppression of macrophage production, such as the effect resulting from the administration of AS-2HS, may selectively decrease rejection responses. Moreover, induction of stem cells production by AS-ACHE will increase the fraction of undifferentiated cells; among those cells are those which do not yet present the tissue compatibility antigens responsible for the rejection response. Thus, combined treatment with AS-2HS, which suppresses hemopoiesis in general, and AS-ACHE can be useful at the levels of the recipient, the transplanted organ or tissue and, in cases where this is known in advance, also at the donor level. In the latter case, the suggested treatment may create in advance, within the donor, macrophages devoid of the phenotype which is responsible for the rejection process. Precisely modulated quantities of the various antisense oligodeoxynucleotides will be required for these mixture treatment, all according to the therapeutic objectives, the route of administration, and the condition of the patient, when used in vivo. Thus it may be necessary for the attending physician to titer the dosage and modify the route of administration as required to obtain the optimal therapeutic effect. The progress of the therapy can be easily monitored by conventional hematology assays or laboratory cell counts. Suitable starting therapeutic doses can be extrapolated from the in vitro efficacy studies described herein.

An important feature of the present invention is that the oligodeoxynucleotide can be administered by perfusion (for organs) or by simple subcutaneous, intramuscular, intravenous or intraperitoneal injection (for patients) and that their effects last for at least several weeks. The limited toxicity of the $S_3$ antisense oligodeoxynucleotides is of particular importance for their therapeutical uses.

This invention provides pharmaceutical compositions comprising at least one of the antisense oligodeoxynucleotides of this invention, or mixtures of at least two of said oligodeoxynucleotides, and physiologically acceptable carriers, exipients or stabilizers, usually in the form of solutions. Acceptable carriers, exipients are nontoxic to recipients at the dosages and concentrations employed, and include buffers, such as phosphate buffered saline and like physiologically acceptable buffers, and more generally all suitable carriers known in the art. The compositions may further optionally contain physiologically acceptable additives such as anioxidants; mono- and disaccharides; salt-forming counterions such as sodium and/or nonionic surfactants. Sustained release compositions are also contemplated within the scope of this application. These may include semipermeable polymeric matrices in the form of shaped articles such as films or microcapsules. The antisense oligodeoxynucleotides and compositions of the invention must be sterile.

EXAMPLES

(I) Materials and Methods (1) Synthesis of Antisense olicodeoxvnucleotides

Oligodeoxynucleotides were synthesized on an Applied Biosystems 380B DNA synthesizer using phosphoramidites from the same company according to the manufacturer's instructions. They were purified by reverse phase HPLC on a Waters dual pump 6000A system in combination with a Waters automated gradient controller and a model 481 UV spectrophotometer operated at 260 nm with the 5'-protecting dimethoxytrityl group still attached to the oligodeoxynucleotides. This was removed by standard treatment with 80% aqueous acetic acid. The oligodeoxynucleotides obtained were checked for purity again by HPLC. To incorporate the phosphorothioate groups, the oxidation step employing iodine was replaced by reaction with 3H-1,2-benzodithiol-3-one 1,1-dioxide [Iyer, R. P., et al., J. Org. Chem. 55:4693–4699 (1990)]. This treatment protects the oligodeoxynucleotides against nuclease (Eckstein, F., Ann. Rev. Biochem., 54:367–402 (1985); Spitzer, F. and Eckstein, F., Nucleic Acids Res., 18:11691–11704 (1988)] and prolongs their duration in vivo [Woolf, T. M., et al., Nucleic Acids Res., 18:1763–1769 (1990); Shaw, J. P., et al., Nucleic Acids Res., 19:747–750 (1991)]. Wherever partial protection was required, reaction with 3H-1,2-benzodithiol-3-one 1,1-dioxide was performed for the first three steps only, after which regular synthesis was continued. The resultant partially protected oligodeoxynucleotides were therefore blocked by phosphorothioate groups only in the last three internucleotidic bonds at their 3'-terminus. The antisense oligodeoxynucleotides employed were AS-ACHE (5'-CTGCGGGGCCTCAT-3'; SEQ ID NO:2) and AS-BCHE (5'-GACTTTGCTATGCAT-3'; SEQ ID NO:3), designed to complement the initiator AUG domain in AChEmRNA [Soreq et al., (1990) ibid.] and BuChEmRNA [Prody et al., (1987) ibid.], respectively. Also employed were AS-CHED (5'-TTTTCCCCAGTCAAT-3'; SEQ ID NO:4), directed against a 5'-region in the human CHED gene [Lapidot-Lifson, Y., et al., Proc. Natl. Acad. Sci. USA, 89:579–583 (1992)] and AS-2HS (5'-GGTATAATCTTCCAT-3'; SEQ ID NO:1) designed to complement the initiator AUG codon in the human cdc2 HS kinase mRNA [Nurse, Nature (1986)].

The antisense oligodeoxynucleotides were kept in 4 mM concentration at $-20°$ C. and were diluted in phosphate buffered saline (PBS) prior to their administration to mice.

(2) In vivo administration

Intraperitoneal injection of AS-CHE and AS-cdc2 oligodeoxynucleotides was performed using a Hamilton syringe. Amounts were calculated according to previous experiments in cell cultures [Patinkin et al., (1990); Lapidot-Lifson et al., (1992)] so that the final concentration of the AS-CHEs reached 5 $\mu$g/gr. weight and the injected volume did not exceed 10 $\mu$l/gr. weight. No toxicity effects were observed on the injected mice, all of which appeared to behave normally and displayed no weight losses. Whenever higher concentrations were used, these are mentioned and the administration procedure remained the same.

(3) Transcription vectors for in vitro synthesis of human AChEcRNA and BuChEcRNA.

Human AChEcDNA (1.5 kb long; clone no. hFEL, Soreq et al., 1990) was subcloned at EcoRI sites into the pGEM7ZF(+) plasmid (Promega) containing the RNA polymerase binding sites from T7 and SP6 bacteriophages. In vitro RNA transcription with SP6 or T7 RNA polymerases was used to produce antisense AChEcRNA or sense AChEmRNA, respectively. Human BuChEcDNA (2.2 kb long; Soreq et al., 1989) was subcloned in PstI/EcoRV restriction sites into the Bluescript SK(+) plasmid (Stratagene) carrying the RNA polymerase binding sites from T7 and T3 bacteriophages. In vitro RNA transcription with T7 and T3 RNA polymerase was employed to produce from this vector "antisense" BuChEcRNA and "sense" BuChEmRNA, respectively.

(4) Preparation of riboprobes for in situ hybridization.

[$^{35}$S] labeled in vitro RNA transcripts ($10^7$ cpm/$\mu$g) were produced using the Amersham RPN 2006 kit and RNA polymerases from Boehringer (Mannheim), using linearized plasmids digested with Hind III, Xho I for the sense and antisense AChE RNA probes and with Apa I, Sma I for the sense and antisense BuChE RNA transcripts, respectively, all according to the manufacturers' instructions. Radiolabeled probes were subjected to alkaline hydrolysis for 20 minutes. The resultant 200–400 bases long fragments were separated from unincorporated nucleotides by Sepahdex column chromatography according to [Wilkinson, D. G., et al., Cell 50:79–88 (1987)]. See FIG. 1.

(5) Tissue preparation and in situ hybridization

Bone marrow was squeezed from dissected femur bones of sacrificed 6 weeks old female mice anesthesized with ether and was smeared as single cell layers on microscope slides coated with 3-aminopropyltriethozysilane (TESPA, Sigma), to prevent loss of cells during the experimental procedure [Rentrop, M., et al., Histochemical Journal 18:271–276 (1986)]. Slides were dried at room temperature for 2 hours, fixed in 4% paraformaldehyde (20 min. at room temperature), washed with 3x and twice 1x phosphate buffered saline, dehydrated through ethanol series, air dried and stored at $-20°$ C. for up to 2 weeks [Hogan, B., et al., A Laboratory Manual, Cold Spring Harbor Laboratory (1986)]. For in situ hybridization slides went through refixation, 0.2M HCl incubation for 20 min. to reduce non-specific probe binding, proteinase K treatment, acetylation and dehydration as described [Rangini, Z., et al., Mechanisms of Development, 35:13–24 (1991)]. Hybridization was performed in the presence of [$^{35}$S]-CHERNA (approx. $1 \times 10^{-7}$ cpm per slide) according to Rangini et al., (1991) except that no thio-ATP was added. Exposure was for 6 weeks. Counter-staining was made with May- Grunwald Giemsa.

(6) microscopal image analysis and statistical data management.

The in situ hybridization results were analysed using a Nikon Microphot microscope equipped with a single slide automatic stage, automatic focus and 60× plan apo oil immersion objective and connected through an interface to a Magiscan Image Analysis microscope controller (Applied Imaging International Ltd, Dukesway, U.K.). Image analysis was carried out by the software package "GENIAS", which counts silver grains, measures cell parameters, and evaluates association of grains with cells. Data management was then performed using the "RESULTS" program, which examines the statistical significance of data obtained from "GENIAS" and subjects area and perimeter measurements to various statistical hypothesis tests (Applied Imaging, U.K.). Briefly, monochromatic images of the examined megakaryocytes were captured using a red filter to improve the contrast. Since the silver grains and cells were at different focal planes, the grains were focussed accurately as their best resolution was required. Grain counts were detected automatically based on their darkness, and high frequency noise information included in the grain image was automatically deleted. Cell borders to be measured were manually delineated, after which grains were counted and measured separately for each cell. Background grain density was measured in parallel and subtracted from the experimental results. Collected data included cell counts and parameters (measured cell areas), number of grains per cell and per unit area and the statistical significance of variations between these parameters. Presented data are average results for separate in vivo treatments, with approximately 40 megakaryocytes at different developmental stages analysed with each of the ChEcRNA probes in bone marrow preparations from four different mice/treatment.

(7) Differential cell analysis of antisense oligonucleotide treated, semi-solid bone marrow cultures.

To grow CFU-MEG colonies, bone marrow cells from the femur and tibia of 8–12 week-old endotoxin-resistant C3H/HeJ mice were cultured in LPM synthetic medium (Biological Industries, Beit HaEmeK, Israel) containing 10% conditioned medium for WEHI-3 cells as a source for interleukin 3 (IL3), 1% BSA, $10^{-4}$M thioglycerol and 1% methylcellulose (megakaryocytopoietic conditions -CFU-MEG).

To obtain erythropoietic conditions and grow CFU-GEMM colonies, $2.8 \times 10^{-4}$M iron-saturated human transferrin and 2 units of erythropoietin (EPO, 1,000 U/mg/ml) were added (CFU-GEMM conditions).

For both culture types, $0.5$–$1.0 \times 10^5$ cells/ml were plated in 35 mm petri dishes (Nunc 1008), or 24 well tissue culture Costar plates, and incubated 4 or 8 days at 37° C. under 5% $CO_2$ with high humidity for CFU-MEG and CFU-GEMM conditions, respectively. Oligodeoxynucleotides, at the denoted final concentrations of 1–20 $\mu$M, were added upon initiation of cultures.

Colonies grown in serum-free methylcellulose cultures containing sense or antisense oligonucleotides were picked with drawn-out Pasteur pipettes, concentrated (5 min at 500×g) by Cytospin (Shandon, 2) centrifugation in phosphate buffered saline (PBS), stained with May-Grunwald Giemsa and analyzed microscopically. The relative fraction of each cell type represented among the total cells recovered from the noted number of independent experiments were then determined. Satisfactory control experiments revealed distributions which were essentially identical to that observed in control (no oligo) cultures, indicating that there was no nonspecific toxicity. At least 500 cells were counted for each data set.

Also, for each experiment the total number of CFU-GEM or CFU-MEGG was determined in a Zeiss Stereozoom binocular after 4 or 8 days in the presence of the examined oligodeoxynucleotides. Colony counts were plotted, either directly or as percent of the total number of colonies in control, untreated cultures. Data represent average of at least three independent experiments ± Standard Evaluation of the Mean (S.E.M.) in each case, unless otherwise noted.

(II) Experiments and Results (1) Concentration dependence of the AS-oliaodeoxynucleotides and their toxicity levels.

All pink or red CFU-GEMM colonies, $\geq 0.5$ mm in diameter, of a given plate are picked with a micropipette, washed in PBS and cytocentrifuged. The CFU-GEMM colonies constitute about 90% of the total colonies present. Cells are stained with May-Grunwald Giemsa and at least 1,000 cells counted per a given experimental condition. Both early erythroblasts and megakaryocytoblasts are small deeply staining cells with very large nuclei and very narrow rims of cytoplasm. They are distinguished from one another by indirect immunocytochemical staining with 1:1,000 dilution of human anti-GPIIb/IIIa Ab (a gift from Barry S. Coller, Stonybrook, N.Y.), followed by a 1:100 dilution of anti-mouse Ig fluorescein-linked Ab (Amersham International) and direct staining with anti-human Glycophorin-alpha Ab (Immunotech, Marseille). Late erythroblasts were characterized by a white or very light blue cytoplasm surrounding a small dark nucleus.

To examine the concentration dependence of the AS-oligodeoxynucleotide effects and determine their toxicity levels, titration curves were derived for each of the employed oligodeoxynucleotides, using megakaryocytopoietic bone marrow cultures. For this purpose, $IL_3$ treated murine bone marrow cell cultures were grown for 4 days in the presence of increasing concentrations of either fully phosphorothioated (Ts) or partially protected at the last 3' internucleotidic bonds ($S_3$) oligodeoxynucleotides up to 10 $\mu$M final concentration and colony numbers were recorded. All of the Ts oligodeoxynucleotides, blocking CHED, BCHE or 2HS, were found to reduce the colony counts significantly. However, the S-BCHE oligodeoxynucleotide, with no counterpart hybridizable chain in any cell, also reduced colony counts at concentration above 5 $\mu$M, demonstrating a non-specific inhibitory effect of such oligodeoxynucleotides on colony formation in culture. This, in turn, suggested that the inhibitory effects of the anti-sense oligodeoxynucleotides could also include a non-specific inhibitory component. This hypothesis was reinforced by the observation that the $S_3$ oligodeoxynucleotides, having the same nucleotide sequences, were, in general, far less toxic then their $T_S$ counterparts in each of the cultures. The non-specific was thus indicated to be related with the phosphorothioate composition of these oligodeoxynucleotides.

To compare the efficacy of $S_3$ and $T_S$ oligodeoxynucleotides, differential cell counts were taken for the $S_3$ and $T_S$ AS-BCHE oligodeoxynucleotides at the final concentration of 5 $\mu$M. Significant reductions in the fraction of megakaryocytes and a matching increase in macrophages were observed with both oligodeoxynucleotides to comparable extents. FIG. 2B demonstrates representative fields from such cultures, and FIG. 3 presents the differential cell fractions for 5 $\mu$M $T_S$ BCHE, CHED or 2Hs in the form of a histogram. The differential count analysis demonstrated that each of the examined anti-sense oligodeoxynucleotides, whether $T_S$ or $S_3$, retained its ability to modulate the megakaryocytopoietic process. Thus, the non-specific toxicity effect appeared to be non-selective, affecting all cell lineages. This, in turn, further strengthened the assumption that part of the reduction effect on colony numbers was due to the non-specific inhibition because of the phosphorothioate nature of the anti-sense oligodeoxynucleotides.

(2) Molecular parameters and toxicity of the examined oligodeoxynucleotides.

To search for correlations between the primary nucleotide sequence of the examined oligodeoxynucleotides and their variable toxicity (potency of inhibiting bone marrow colony formation under megakaryocytopoietic conditions) effects, several molecular parameters were determined. These included their melting temperature (Tm), nucleotide composition in percentage, their tendency to form dimers under physiological conditions and the optional loop structures which these oligodeoxynucleotides may form within themselves. In particular, inventors examined the possibility of the four 3'-terminal nucleotides (and hence the last 3 internucleotidic bonds) in these oligodeoxynucleotides to be involved in intramolecular structures. This analysis (FIG. 4) revealed an apparent direct relationship between the ability of the three 3'-terminal internucleotidic bonds to form intramolecular loops and the relative toxicity values of the corresponding AS-oligodeoxynucleotides at 5–10 $\mu$M concentrations. Thus, AS-oligodeoxynucleotides with no tendency for intramolecular looping at their 3' terminus would tend to be less toxic yet similarly effective in cultured cells. It is important to note at this point that studies of others have shown extension in vivo of AS-oligodeoxynucleotides [Agarwal, et al., (1991) ibid.] This process, presumably useful as a scavenging mechanism to remove alien AS-oligonucleotides from the circulation depends on the existence of free 3'-termini in the attached oligonucleotides. Partial phosphorothioate protection at this important position may hence be sufficient to ensure stability of these AS-oligodeoxynucleotides and, in addition, can reduce their non-specific toxicity effects by assisting in natural scavenging of these compounds when not involved in DNA-mRNA hybrids.

(3) Effects of examined oligodeoxynucleotides under megakaryocytopietic and erythropoietic conditions.

Assuming that the above detailed specific AS-oligodeoxynucleotides effects are caused due to damage in cholinergic signalling, parallel oligodeoxynucleotides were prepared according to the 15 nucleotides spanning the region of the AUG codon in the AChE coding sequence [Soreq et al., (1990) ibid.]. Both sense and antisense oligodeoxynucleotides were designed to include three 3'-terminal blocked internucleotidic bonds (i.e. in their $S_3$ form) and their molecular properties were similarly analyzed. The absence of 3'-involvement in intramolecular loops was ensured by computer analysis of the designed oligodeoxynucleotides and prompted further experiments, using these AChE oligodeoxynucleotides in cell cultures, in parallel with the BuChE ones described above.

To deepen the cell culture approach, bone marrow cells were grown either with $IL_3$ alone, (i.e. megakaryocytopoietic conditions, inducing only CFU-MEG colonies) or with the addition of transferrin and erythropoietin as well (i.e. erythropoietic conditions, in which CFU-GEMM colonies may also develop, GEMM implying granulocytes, erythrocytes, macrophages and megakaryocytes).

This composite experiment revealed that in the CFU-MEG cultures, both AS-ACHE and AS-BCHE blocked megakaryocytopoiesis efficiently, however at various efficacies. AS-ACHE (but not S-ACHE) was effective already at 4 $\mu$M concentration, blocking ca. 50% of colonies. In contrast, AS-BCHE blocked only 30% of colony formation at 4 $\mu$M and higher concentrations. In both cases, the sense $S_3$, oligodeoxynucleotides were-totally non-toxic, suggesting that the inhibition effects exerted by the A.S-oligodeoxynucleotides were selective and specific.

In CFU-GEMM cultures, opposing effects were observed for AS-ACHE, which induced a dramatic 3-fold increase in colony counts at the final concentration of 10 $\mu$M. In contrast, As-BCHE was ineffective at this concentration. Interstingly, CFU-GEMM colonies grown in the presence of AS-ACHE appeared smaller in size and composed of many more small cells than the parallel colonies grown under control conditions. Total cell counts for these colonies further revealed 2-fold increase in cell numbers for AS-ACHE colonies as compared with controls.

FIG. 5 presents the titration effects of the ChE-related examined oligodeoxynucleotides under CFU-GEMM forming conditions.

(4) Determination of the specificity of the examined oligodeoxynucleotides by differential colony counts.

The specificity of the oligodeoxynucleotide effects was further examined by comparable differential counts. The change in colony counts observed for AS-ACHE as compared with S-ACHE was thus shown to be accompanied by a selective decrease in megakaryocytes under CFU-MEG conditions and reduction in both megakaryocytes and erythrocytes under CFU-GEMM conditions, all at the very low 2 $\mu$M final concentration. In parallel, AS-BCHE but not S-BCHE at 4 $\mu$M concentration reduced megakaryocytopoiesis under both sets of experimental conditions. Cultures grown in the absence of any oligodeoxynucleotide (none) served for controls. FIGS. 6 (A1, A2) present these cell fractions in the form of histograms. It should also be noted that under erythropoietic conditions and at a concentration of 12 $\mu$M, AS-ACHE further decreases the number of erythrocytes and megakaryocytes, as observed in the cell culture experiments.

(5) Effect of AS-ACHE on bone marrow cells in vivo.

To extend these studies into the in vivo situation, laboratory grown wild mice were injected intraperitoneally 48 hr. postnatal with 5 or 25 $\mu$g/gr of the $T_S$ oligodeoxynucleotides dissolved in PBS. 3 weeks after, bone marrow was examined. FIG. 7 depicts a representative micrograph of the bone marrow smears.

Apparently, erythrocyte fractions were reduced also in vivo, whereas lymphocytes (including stem cells) increased considerably. S-ACHE remained ineffective.

Megakaryocytes could not be counted because of the small in vivo counts, however photography revealed an in vivo reduction in their numbers as well. However, while the in vivo effects appeared to be relatively moderate as compared with those measured under culture conditions, these findings demonstrate that the AS-ACHE effects measured in vitro were indeed true effects, reflecting the effect of this oligodeoxynucleotide under in vivo conditions as well.

It should be noted that the fraction defined as "lymphocytes" in the in vivo analyses of bone marrow smears includes proliferating stem cells. However, the in vivo approach does not allow for counting of dividing stem cells. In contrast, cell counts and differential cell compositions in culture experiments clearly showed increased fractions of young, apparently dividing cells. Thus, the culture experiments and the in vivo ones are complementary to each other in providing important information on the duration of the treatment, its effectiveness and its specificity. In particular, the ability of the AS-oligodeoxynucleotides to enhance cell division is important.

(6) Increased ChEmRNA levels through megakaryocytes maturation in untreated mice In situ hybridization was performed with bone marrow smears from Sabra mice using antisense ChEcRNA and sense ChEmRNA probes transcribed from the pGEM-7ZF (+) AChEcDNA plasmid and the Bluescript SK(+) BuCh-EcDNA plasmid (FIG. 1). The smeared bone marrow cells included lymphoid and erythroid cells, as well as megakaryocytes in different developmental stages. Significant labeling with the antisense probe appeared only over megakaryocytes, suggesting intensive expression of the CHE genes in these cells. Labeling with the control, sense probes, was negligible throughout the smears, demonstrating the specificity of the hybridization reactions. Immature megakaryocytes, with up to 4 nuclei, appeared generally unlabeled. Distribution of silver grains reflecting ChEmRNA levels in mouse megakaryocytes at three later differentiation stages was determined following Magiscan classification, into:

(A) Promegakaryocytes of 14–20 μm cell diameter with 4–8 nuclei and smaller cytoplasm than nucleus;

(B) >20 μm diameter intermediate cells, with 8–16 nuclei and cytoplasm equal in size to nucleus;

(C) Mature >20 μm cell diameter megakarcyocytes with 16–64 nuclei and abundant cytoplasm [Courtney, M., et al., Blood, 77: 560–568 (1991)].

FIG. 8 demonstrates high intensity AChEcRNA labeling as compared with lower density BuChEcRNA labeling and no labeling with sense AChEmRNA or BuChEmRNA in untreated animals. It should be noted that RNase treatment prior to the in situ hybridization abolishes all labeling in this procedure (not shown), providing evidence for the RNA-dependence of these reactions.

Megakaryocytes belonging to each of the above sub-types were further divided into sub-groups according to their radiolabel intensities (up to 20 grains, between 20 and 40, etc). The variability in AChEcRNA grain no./cell was found to increase with megakaryocytes development (FIG. 9A–B), in accordance with the longer life time of mature megakaryocites as compared with their progenitors (Mazur, 1987).

(7) Altered CHEmRNA levels in mice infected with anti-sense oligodeoxynucleotides.

To selectively interfere with the expression of the CHE genes, 4 different mice were injected once with 5 μg/gr weight of 15-mer antisense phosphorothioate oligodeoxy-nucleotides complementary to the initiator AUG domains in AChEmRNA or BuChEmRNA, respectively, or with PBS for controls. Three weeks following the injection, bone marrow smears were prepared from all of these mice. Each smear was divided into separate parts which were hybridized with one of the two ChEcRNA probes. Following 6 weeks of exposure to emulsion autoradiography, slides were developed to create silver grains over cells containing ChEcRNAs. Labeling decreased in bone marrow smears prepared from AS-ACHE and, more effectively, in AS-BuCHE treated mice. FIG. 10 displays representative photographs demonstrating the variable ChEmRNA labeling in the differently treated mice.

Computerized image analysis and statistical processing of the silver grain counts (at least 40 cells/sample for 4 mice and two probes per treatment), revealed different accumulation patterns for the two ChEmRNAs in the AS-CHE injected animals as compared with control, PBS-injected mice.

In control mice, AChEmRNA levels per cell increased by 20-fold from the promegakaryocyte stage to mature megakaryocytes, while the lower BuChEmRNA levels could only be detected in intermediate and mature megakaryocytes and remained unaltered in these two stages of megakaryocytes development (FIG. 11).

Computerized image analysis and processing of the silver grain counts (at least 40 cells/sample for 4 mice and two probes per treatment), demonstrated differently suppressed developmental patterns for the two ChEmRNA in the AS-CHE injected animals as compared with control, PBS-injected mice. Three weeks following the treatment, AChEmRNA and BuChEmRNA levels were reduced by approximately 62 and 30%, respectively, in mature megakaryocytes from AS-ACHE-treated mice. In contrast, AS-BCHE treatment reduced both AChEmRNA and BuChEmRNA levels by about 66% (FIG. 11). Statistical analysis revealed for these values a bidirectoinal variance at a significance level of 5% [Hoel, P. G., Elementary Statistics, 4th Ed., John Wiley & Sons, Inc. New York London (1976)]. Furthermore, the suppressed levels of mRNAs within megakaryocytes at different developmental stages appeared to significantly dependent on the nature of the AS-oligodeoxynucleotides treatment in different mice as shown by the averaged slopes of the curves in FIG. 11. Thus, AChEmRNA was more significantly suppressed when AS-ACHE was injected than with AS-BCHE, and the effect of AS-BCHE upon BuChEmRNA levels was more conspicuous after injection of AS-BCHE than with AS-ACHE. Altogether, these data demonstrate the in vivo effectiveness, the long term duration and the interrelationship between the effects of the two AS-CHE drugs.

(8) AS-CHEs modulate megakaryocytes development in vivo.

The total no. of megakaryocytes in each of the bone marrow smears from the different mice was found to be somewhat higher in AS-ACHE treated mice (N=78.2±18.6) as compared with controls (N=66.5±4.9). In contrast, the no. of megakaryocytes per smear in AS-BCHE treated mice was significantly lower, with very limited variability between the different mice (N=57.7±1.1). Differential cell counts of bone marrow megakaryocyte populations were further performed using the Magiscan image analysis system (Materials and Methods (6)). Intermedial cells represented approximately 85% of the total no. of megakaryocytes in control mice, with mature cells accounting for about 10% and immature and promegakaryocytes composing the remaining minor fractions (FIG. 12A). Reduced numbers of intermedial cells and enlarged fractions of both immature and mature megakaryocytes were observed in AS-ACHE treated mice (FIG. 12B), while AS-BCHE treated mice displayed apparently normal composition of megakaryocyte subtypes (FIG. 12C). Thus, the AS-ACHE treatment induced a general enhancement in megakaryocytopoiesis, accompanied by distortion of the megakaryocytopoietic process in vivo. In contrast, AS-BCHE suppressed megakaryocytopoiesis without affecting the differential cell counts, suggesting that it either blocks the early stages of megakaryocytopoiesis or that it similarly suppresses all stages.

(9) Primary AS-Oligodeoxynucleotides Suppression of One ChEmRNA Selectively Leads to Secondary Inhibition of Its Counterpart ChEmRNA Type.

Bone marrow cDNA from AS-ACHE-treated and control, PBS-injected mice was subjected to direct amplification using polymerase chain reaction (PCR) with mouse actin primers. This analysis, displayed in FIG. 13, revealed apparently similar levels of the amplified actin cDNA fragments in treated and control mice, demonstrating that the AS-oligodeoxynucleotide treatment did not generally abolish transcription in the bone marrow. Differential cell counts in the analyzed bone marrow smears further revealed apparently normal composition of ca. 40% erythroid cells, 27% granulocytes, 17% lymphocytes and stem cells, 13–14% myeloid cells and 2–3% eosinophils for several of the AS-ACHE-treated and control animals. Peripheral automated blood profiles of these animals displayed ca. 75% lymphocytes, 18% neutrophils, 5% monocytes and 2% eosinophils, a normal composition characteristic of healthy animals, for both treated and control mice. Thus, the AS-oligodeoxynucleotide treatment was apparently harmless for hemopoietic composition at the time of this analysis, suggesting that the indirect suppression of BuChEmRNA by AS-ACHE and the yet more efficient suppression of AChEmRNA by AS-BCHE reflects selectively induced secondary effects of each of these AS-oligodeoxynucleotide treatments.

(10) cytoplasmic accumulation of AS-oligodeoxynucleotides indicates post-transcriptional regulation as their primary role.

Referring to FIG. 14, comparison of bright field and fluorescence photography revealed an apparent relationship between the abundance of cytoplasm and the brightness of the fluorescent signal. Thus, mature megakaryocytes accumulated relatively large amounts of the FITC-labeled AS-CHED (A), whereas young megakaryocytes displayed significantly lower intensities of fluorescence (B) and polymorphonuclear cells yet lower signals. Both young and mature megakaryocytes and polymorphonuclear cells were capable of taking up the FITC-AS-CHED with apparently similar efficiencies, suggesting that the presumed receptor sites enabling this uptake process appear early in the development of both these cell types and are expressed throughout their life span. Most importantly, this analysis demonstrated nuclear exclusion of the accumulated FITC-AS-CHED (which was $S_3$ in its phosphorothioate composition). Thus, most of the uptaken compound accumulated in the cytoplasm of the treated cells, where it could hybridized with the mature CHED mRNA species but not with the CHED gene and/or with its nascent, non-processed nuclear mRNA transcript. Moreover, cytoplasmic FITC fluorescence could also be detected in megakaryocytes after 4 days in culture (D), indicating that the AS-oligodeoxynucleotides remain in this subcellular site for at least several days. The specificity of the fluorescence signals, in turn, was proved by the absence of such signals in young and developed megakaryocytes, polymorphonuclear cells and macrophages in culture to which no FITC-oligodeoxynucleotides were added (E,F).

In addition to the cytoplasmic signals, the FITC-labeled AS-oligodeoxynucleotide created fluorescent signals larger over the cell surface, so that the cell diameter appeared larger under fluorescent than with bright field photography (compare A–D in FIG. 14). This could imply a continuous occupation of all available receptor sites over the surface of treated cells for the entire duration of the experiment.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: YES ( x i ) SEQUENCE DESCRIPTION: SEQ ID NO:1:

G G T A T A A T C T  T C C A T					1 5

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: YES ( x i ) SEQUENCE DESCRIPTION: SEQ ID NO:2:

C T G C G G G G G C  C T C A T					1 5

( 2 ) INFORMATION FOR SEQ ID NO:3:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: other nucleic acid ( i v ) ANTI-SENSE: YES ( x i ) SEQUENCE DESCRIPTION: SEQ ID NO:3:

| GACTTTGCTA TGCAT | 15 |

( 2 ) INFORMATION FOR SEQ ID NO:4:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: other nucleic acid ( i v ) ANTI-SENSE: YES ( x i ) SEQUENCE DESCRIPTION: SEQ ID NO:4:

| TTTTCCCCAG TCAAT | 15 |

( 2 ) INFORMATION FOR SEQ ID NO:5:

( i ) SEQUENCE CHARACTERISTICS:
  ( A ) LENGTH: 2256 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
  ( A ) ORGANISM: Homo sapiens ( i x ) FEATURE:
  ( D ) OTHER INFORMATION: /note= "Splice variant: Exons 1, 2, 3, 4 and 6"

( x i ) SEQUENCE DESCRIPTION: SEQ ID NO:5:

| CCTCTCTCCC | CTCATCTTTG | CCAACCTGCC | CCACCTCCTC | TGCAGCTGAG | CGATAACCCT | 60 |
| TGGGCCGACA | GTGCCCTAAT | CTCCTCCCTC | CTGGCTTCTC | GACCGACCCT | TCACCCTTTC | 120 |
| CCTTTCTTTC | TCCCAGCAGA | CGCCGCCTGC | CCTGCAGCCA | TGAGGCCCCC | GCAGTGTCTG | 180 |
| CTGCACACGC | CTTCCCTGGC | TTCCCCACTC | CTTCTCCTCC | TCCTCTGGCT | CCTGGGTGGA | 240 |
| GGAGTGGGGG | CTGAGGGCCG | GGAGGATGCA | GAGCTGCTGG | TGACGGTGCG | TGGGGGCCGG | 300 |
| CTGCGGGGCA | TTCGCCTGAA | GACCCCCGGG | GGCCCTGTCT | CTGCTTTCCT | GGGCATCCCC | 360 |
| TTTGCGGAGC | CACCCATGGG | ACCCCGTCGC | TTTCTGCCAC | CGGAGCCCAA | GCAGCCTTGG | 420 |
| TCAGGGGTGG | TAGACGCTAC | AACCTTCCAG | AGTGTCTGCT | ACCAATATGT | GGACACCCTA | 480 |
| TACCCAGGTT | TTGAGGGCAC | CGAGATGTGG | AACCCCAACC | GTGAGCTGAG | CGAGGACTGC | 540 |
| CTGTACCTCA | ACGTGTGGAC | ACCATACCCC | CGGCCTACAT | CCCCCACCCC | TGTCCTCGTC | 600 |
| TGGATCTATG | GGGGTGGCTT | CTACAGTGGG | GCCTCCTCCT | TGGACGTGTA | CGATGGCCGC | 660 |
| TTCTTGGTAC | AGGCCGAGAG | GACTGTGCTG | GTGTCCATGA | ACTACCGGGT | GGGAGCCTTT | 720 |
| GGCTTCCTGG | CCCTGCCGGG | GAGCCGAGAG | GCCCCGGGCA | ATGTGGGTCT | CCTGGATCAG | 780 |

| | | | | | |
|---|---|---|---|---|---|
|AGGCTGGCCC|TGCAGTGGGT|GCAGGAGAAC|GTGGCAGCCT|TCGGGGGTGA|CCCGACATCA 840|
|GTGACGCTGT|TTGGGGAGAG|CGCGGGAGCC|GCCTCGGTGG|GCATGCACCT|GCTGTCCCCG 900|
|CCCAGCCGGG|GCCTGTTCCA|CAGGGCCGTG|CTGCAGAGCG|GTGCCCCCAA|TGGACCCTGG 960|
|GCCACGGTGG|GCATGGGAGA|GGCCCGTCGC|AGGGCCACGC|AGCTGGCCCA|CCTTGTGGGC 1020|
|TGTCCTCCAG|GCGGCACTGG|TGGGAATGAC|ACAGAGCTGG|TAGCCTGCCT|TCGGACACGA 1080|
|CCAGCGCAGG|TCCTGGTGAA|CCACGAATGG|CACGTGCTGC|CTCAAGAAAG|CGTCTTCCGG 1140|
|TTCTCCTTCG|TGCCTGTGGT|AGATGGAGAC|TTCCTCAGTG|ACACCCAGA|GGCCCTCATC 1200|
|AACGCGGGAG|ACTTCCACGG|CCTGCAGGTG|CTGGTGGGTG|TGGTGAAGGA|TGAGGGCTCG 1260|
|TATTTTCTGG|TTTACGGGGC|CCCAGGCTTC|AGCAAAGACA|ACGAGTCTCT|CATCAGCCGG 1320|
|GCCGAGTTCC|TGGCCGGGGT|GCGGGTCGGG|GTTCCCCAGG|TAAGTGACCT|GGCAGCCGAG 1380|
|GCTGTGGTCC|TGCATTACAC|AGACTGGCTG|CATCCCGAGG|ACCCGGCACG|CCTGAGGGAG 1440|
|GCCCTGAGCG|ATGTGGTGGG|CGACCACAAT|GTCGTGTGCC|CCGTGGCCCA|GCTGGCTGGG 1500|
|CGACTGGCTG|CCCAGGGTGC|CCGGGTCTAC|GCCTACGTCT|TTGAACACCG|TGCTTCCACG 1560|
|CTCTCCTGGC|CCCTGTGGAT|GGGGGTGCCC|CACGGCTACG|AGATCGAGTT|CATCTTTGGG 1620|
|ATCCCCCTGG|ACCCCTCTCG|AAACTACACG|GCAGAGGAGA|AAATCTTCGC|CCAGCGACTG 1680|
|ATGCGATACT|GGGCCAACTT|TGCCCGCACA|GGGGATCCCA|ATGAGCCCCG|AGACCCCAAG 1740|
|GCCCCACAAT|GGCCCCCGTA|CACGGCGGGG|GCTCAGCAGT|ACGTTAGTCT|GGACCTGCGG 1800|
|CCGCTGGAGG|TGCGGCGGGG|GCTGCGCGCC|CAGGCCTGCG|CCTTCTGGAA|CCGCTTCCTC 1860|
|CCCAAATTGC|TCAGCGCCAC|CGACACGCTC|GACGAGGCGG|AGCGCCAGTG|GAAGGCCGAG 1920|
|TTCCACCGCT|GGAGCTCCTA|CATGGTGCAC|TGGAAGAACC|AGTTCGACCA|CTACAGCAAG 1980|
|CAGGATCGCT|GCTCAGACCT|GTGACCCGG|CGGGACCCCC|ATGTCCTCCG|CTCCGCCCGG 2040|
|CCCCCTAGCT|GTATATACTA|TTTATTTCAG|GGCTGGGCTA|TAACACAGAC|GAGCCCAGA 2100|
|CTCTGCCCAT|CCCCACCCCA|CCCCGACGTC|CCCCGGGGCT|CCCGGTCCTC|TGGCATGTCT 2160|
|TCAGGCTGAG|CTCCTCCCCG|CGTGCCTTCG|CCCTCTGGCT|GCAAATAAAC|TGTTACAGGC 2220|
|CAAAAAAAA|AAAAAAAAA|AAAAAAAAA|AAAAA| | 2256|

( 2 ) INFORMATION FOR SEQ ID NO:6:

( i ) SEQUENCE CHARACTERISTICS:
        ( A ) LENGTH: 3096 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 160..1959
        ( D ) OTHER INFORMATION: /note= "Splice variant: Exons 1, 2,
            3, 4, 5 and the translated portion of Intron 4
            ( r e a d t h r o u g h )"

( x i ) SEQUENCE DESCRIPTION: SEQ ID NO:6:

| | | | | | |
|---|---|---|---|---|---|
|CCTCTCTCCC|CTCATCTTTG|CCAACCTGCC|CCACCTCCTC|TGCAGCTGAG|CGATAACCCT 60|

-continued

| | | | | | |
|---|---|---|---|---|---|
| TGGGCCGACA | GTGCCCTAAT | CTCCTCCCTC | CTGGCTTCTC | GACCGACCCT | TCACCCTTTC | 120
| CCTTTCTTTC | TCCCAGCAGA | CGCCGCCTGC | CCTGCAGCCA | TGAGGCCCCC | GCAGTGTCTG | 180
| CTGCACACGC | CTTCCCTGGC | TTCCCCACTC | CTTCTCCTCC | TCCTCTGGCT | CCTGGGTGGA | 240
| GGAGTGGGGG | CTGAGGGCCG | GGAGGATGCA | GAGCTGCTGG | TGACGGTGCG | TGGGGGCCGG | 300
| CTGCGGGGCA | TTCGCCTGAA | GACCCCCGGG | GGCCCTGTCT | CTGCTTTCCT | GGGCATCCCC | 360
| TTTGCGGAGC | CACCCATGGG | ACCCCGTCGC | TTTCTGCCAC | CGGAGCCCAA | GCAGCCTTGG | 420
| TCAGGGGTGG | TAGACGCTAC | AACCTTCCAG | AGTGTCTGCT | ACCAATATGT | GGACACCCTA | 480
| TACCCAGGTT | TTGAGGGCAC | CGAGATGTGG | AACCCCAACC | GTGAGCTGAG | CGAGGACTGC | 540
| CTGTACCTCA | ACGTGTGGAC | ACCATACCCC | CGGCCTACAT | CCCCCACCCC | TGTCCTCGTC | 600
| TGGATCTATG | GGGGTGGCTT | CTACAGTGGG | GCCTCCTCCT | TGGACGTGTA | CGATGGCCGC | 660
| TTCTTGGTAC | AGGCCGAGAG | GACTGTGCTG | GTGTCCATGA | ACTACCGGGT | GGGAGCCTTT | 720
| GGCTTCCTGG | CCCTGCCGGG | GAGCCGAGAG | GCCCCGGGCA | ATGTGGGTCT | CCTGGATCAG | 780
| AGGCTGGCCC | TGCAGTGGGT | GCAGGAGAAC | GTGGCAGCCT | TCGGGGGTGA | CCCGACATCA | 840
| GTGACGCTGT | TTGGGGAGAG | CGCGGGAGCC | GCCTCGGTGG | GCATGCACCT | GCTGTCCCCG | 900
| CCCAGCCGGG | GCCTGTTCCA | CAGGGCCGTG | CTGCAGAGCG | GTGCCCCCAA | TGGACCCTGG | 960
| GCCACGGTGG | GCATGGGAGA | GGCCCGTCGC | AGGGCCACGC | AGCTGGCCCA | CCTTGTGGGC | 1020
| TGTCCTCCAG | GCGGCACTGG | TGGGAATGAC | ACAGAGCTGG | TAGCCTGCCT | TCGGACACGA | 1080
| CCAGCGCAGG | TCCTGGTGAA | CCACGAATGG | CACGTGCTGC | CTCAAGAAAG | CGTCTTCCGG | 1140
| TTCTCCTTCG | TGCCTGTGGT | AGATGGAGAC | TTCCTCAGTG | ACACCCCAGA | GGCCCTCATC | 1200
| AACGCGGGAG | ACTTCCACGG | CCTGCAGGTG | CTGGTGGGTG | TGGTGAAGGA | TGAGGGCTCG | 1260
| TATTTTCTGG | TTTACGGGGC | CCCAGGCTTC | AGCAAAGACA | ACGAGTCTCT | CATCAGCCGG | 1320
| GCCGAGTTCC | TGGCCGGGGT | GCGGGTCGGG | GTTCCCCAGG | TAAGTGACCT | GGCAGCCGAG | 1380
| GCTGTGGTCC | TGCATTACAC | AGACTGGCTG | CATCCCGAGG | ACCCGGCACG | CCTGAGGGAG | 1440
| GCCCTGAGCG | ATGTGGTGGG | CGACCACAAT | GTCGTGTGCC | CCGTGGCCCA | GCTGGCTGGG | 1500
| CGACTGGCTG | CCCAGGGTGC | CCGGGTCTAC | GCCTACGTCT | TTGAACACCG | TGCTTCCACG | 1560
| CTCTCCTGGC | CCCTGTGGAT | GGGGGTGCCC | CACGGCTACG | AGATCGAGTT | CATCTTTGGG | 1620
| ATCCCCCTGG | ACCCCTCTCG | AAACTACACG | GCAGAGGAGA | AAATCTTCGC | CCAGCGACTG | 1680
| ATGCGATACT | GGGCCAACTT | TGCCCGCACA | GGGGATCCCA | ATGAGCCCCG | AGACCCCAAG | 1740
| GCCCCACAAT | GGCCCCCGTA | CACGGCGGGG | GCTCAGCAGT | ACGTTAGTCT | GGACCTGCGG | 1800
| CCGCTGGAGG | TGCGGCGGGG | GCTGCGCGCC | CAGGCCTGCG | CCTTCTGGAA | CCGCTTCCTC | 1860
| CCCAAATTGC | TCAGCGCCAC | CGGTATGCAG | GGGCCAGCGG | GCAGCGGCTG | GGAGGAGGGG | 1920
| AGTGGGAGCC | CGCCAGGTGT | AACCCCTCTC | TTCTCCCCCT | AGCCTCGGAG | GCTCCCAGCA | 1980
| CCTGCCCAGG | CTTCACCCAT | GGGGAGGCTG | CTCCGAGGCC | CGGCCTCCCC | CTGCCCCTCC | 2040
| TCCTCCTCCA | CCAGCTTCTC | CTCCTCTTCC | TCTCCCACCT | CCGGCGGCTG | TGAACACGGC | 2100
| CTCTTCCCCT | ACGGCCTACA | GGGGCCCCTC | CTCTAATGAG | TGGTAGGACC | TGTGGGAAG | 2160
| GGCCCCACTC | AGGGATCTCA | GACCTAGTGC | TCCCTTCCTC | CTCAAACCGA | GAGACTCACA | 2220
| CTGGACAGGG | CAGGAGGAGG | GGCCGTGCCT | CCCACCCTTC | TCAGGGACCC | CCACGCCTTT | 2280
| GTTGTTTGAA | TGGAAATGGA | AAAGCCAGTA | TTCTTTTATA | AAATTATCTT | TTGGAACCTG | 2340
| AGCCTGACAT | TGGGGGAAGT | GGAGGCCCGG | AAACGGGGTA | GCACCCCAT | TGGGGCTATA | 2400
| ACGGTCAACC | ATTTCTGTCT | CTTCTTTTTC | CCCCAACCTC | CCCCTCCTGT | CCCCTCTGTT | 2460

| | | | | | |
|---|---|---|---|---|---|
| CCCGTCTTCC | GGTCATTCTT | TTCTCCTCCT | CTCTCCTTCC | TGCTGTCCTT | CTCGGCCCCG | 2520 |
| CCTCTGCCCT | CATCCTCCCT | CTCGTCTTTC | GCACATTCTC | CTGATCCTCT | TGCCACCGTC | 2580 |
| CCACGTGGTC | GCCTGCATTT | CTCCGTGCGT | CCTCCCTGCA | CTCATACCCC | CCCTTCAACC | 2640 |
| CGCCCAAATG | TCCGATCCCC | GACCTTCCTC | GTGCCGTCCT | CCCCTCCCGC | CTCGCTGGGC | 2700 |
| GCCCTGGCCG | CAGACACGCT | CGACACGCTC | GACGAGGCGG | AGCGCCAGTG | GAAGGCCGAG | 2760 |
| TTCCACCGCT | GGAGCTCCTA | CATGGTGCAC | TGGAAGAACC | AGTTCGACCA | CTACAGCAAG | 2820 |
| CAGGATCGCT | GCTCAGACCT | GTGACCCGG | CGGGACCCCC | ATGTCCTCCG | CTCCGCCCGG | 2880 |
| CCCCCTAGCT | GTATATACTA | TTTATTTCAG | GGCTGGGCTA | TAACACAGAC | GAGCCCCAGA | 2940 |
| CTCTGCCCAT | CCCCACCCCA | CCCCGACGTC | CCCCGGGGCT | CCCGGTCCTC | TGGCATGTCT | 3000 |
| TCAGGCTGAG | CTCCTCCCCG | CGTGCCTTCG | CCCTCTGGCT | GCAAATAAAC | TGTTACAGGC | 3060 |
| CAAAAAAAAA | AAAAAAAAA | AAAAAAAAA | AAAAA | | | 3096 |

(2) INFORMATION FOR SEQ ID NO:7:

(i) SEQUENCE CHARACTERISTICS:
        (A) LENGTH: 3016 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 160..2010
        (D) OTHER INFORMATION: /note= "Splice Variant: Exons 1, 2, 3, 4, 5 and 6"

(xi) SEQUENCE DESCRIPTION: SEQ ID NO:7:

| | | | | | |
|---|---|---|---|---|---|
| CCTCTCTCCC | CTCATCTTTG | CCAACCTGCC | CCACCTCCTC | TGCAGCTGAG | CGATAACCCT | 60 |
| TGGGCCGACA | GTGCCCTAAT | CTCCTCCCTC | CTGGCTTCTC | GACCGACCCT | TCACCCTTTC | 120 |
| CCTTTCTTTC | TCCCAGCAGA | CGCCGCCTGC | CCTGCAGCCA | TGAGGCCCCC | GCAGTGTCTG | 180 |
| CTGCACACGC | CTTCCCTGGC | TTCCCCACTC | CTTCTCCTCC | TCCTCTGGCT | CCTGGGTGGA | 240 |
| GGAGTGGGGG | CTGAGGGCCG | GGAGGATGCA | GAGCTGCTGG | TGACGGTGCG | TGGGGGCCGG | 300 |
| CTGCGGGGCA | TTCGCCTGAA | GACCCCCGGG | GGCCCTGTCT | CTGCTTTCCT | GGGCATCCCC | 360 |
| TTTGCGGAGC | CACCCATGGG | ACCCCGTCGC | TTTCTGCCAC | CGGAGCCCAA | GCAGCCTTGG | 420 |
| TCAGGGGTGG | TAGACGCTAC | AACCTTCCAG | AGTGTCTGCT | ACCAATATGT | GGACACCCTA | 480 |
| TACCCAGGTT | TTGAGGGCAC | CGAGATGTGG | AACCCCAACC | GTGAGCTGAG | CGAGGACTGC | 540 |
| CTGTACCTCA | ACGTGTGGAC | ACCATACCCC | CGGCCTACAT | CCCCACCCC | TGTCCTCGTC | 600 |
| TGGATCTATG | GGGGTGGCTT | CTACAGTGGG | GCCTCCTCCT | TGGACGTGTA | CGATGGCCGC | 660 |
| TTCTTGGTAC | AGGCCGAGAG | GACTGTGCTG | GTGTCCATGA | CTACCGGGT | GGGAGCCTTT | 720 |
| GGCTTCCTGG | CCCTGCCGGG | GAGCCGAGAG | GCCCCGGGCA | ATGTGGGTCT | CCTGGATCAG | 780 |
| AGGCTGGCCC | TGCAGTGGGT | GCAGGAGAAC | GTGGCAGCCT | TCGGGGGTGA | CCCGACATCA | 840 |
| GTGACGCTGT | TTGGGGAGAG | CGCGGGAGCC | GCCTCGGTGG | GCATGCACCT | GCTGTCCCCG | 900 |
| CCCAGCCGGG | GCCTGTTCCA | CAGGGCCGTG | CTGCAGAGCG | GTGCCCCCAA | TGGACCCTGG | 960 |

| | | | | | | |
|---|---|---|---|---|---|---|
| GCCACGGTGG | GCATGGGAGA | GGCCCGTCGC | AGGGCCACGC | AGCTGGCCCA | CCTTGTGGGC | 1020 |
| TGTCCTCCAG | GCGGCACTGG | TGGGAATGAC | ACAGAGCTGG | TAGCCTGCCT | TCGGACACGA | 1080 |
| CCAGCGCAGG | TCCTGGTGAA | CCACGAATGG | CACGTGCTGC | CTCAAGAAAG | CGTCTTCCGG | 1140 |
| TTCTCCTTCG | TGCCTGTGGT | AGATGGAGAC | TTCCTCAGTG | ACACCCAGA | GGCCCTCATC | 1200 |
| AACGCGGGAG | ACTTCCACGG | CCTGCAGGTG | CTGGTGGGTG | TGGTGAAGGA | TGAGGGCTCG | 1260 |
| TATTTTCTGG | TTTACGGGGC | CCCAGGCTTC | AGCAAAGACA | ACGAGTCTCT | CATCAGCCGG | 1320 |
| GCCGAGTTCC | TGGCCGGGGT | GCGGGTCGGG | GTTCCCCAGG | TAAGTGACCT | GGCAGCCGAG | 1380 |
| GCTGTGGTCC | TGCATTACAC | AGACTGGCTG | CATCCCGAGG | ACCCGGCACG | CCTGAGGGAG | 1440 |
| GCCCTGAGCG | ATGTGGTGGG | CGACCACAAT | GTCGTGTGCC | CCGTGGCCCA | GCTGGCTGGG | 1500 |
| CGACTGGCTG | CCCAGGGTGC | CCGGGTCTAC | GCCTACGTCT | TTGAACACCG | TGCTTCCACG | 1560 |
| CTCTCCTGGC | CCCTGTGGAT | GGGGGTGCCC | CACGGCTACG | AGATCGAGTT | CATCTTTGGG | 1620 |
| ATCCCCCTGG | ACCCCTCTCG | AAACTACACG | GCAGAGGAGA | AAATCTTCGC | CCAGCGACTG | 1680 |
| ATGCGATACT | GGGCCAACTT | TGCCCGCACA | GGGGATCCCA | ATGAGCCCG | AGACCCCAAG | 1740 |
| GCCCCACAAT | GGCCCCCGTA | CACGGCGGGG | GCTCAGCAGT | ACGTTAGTCT | GGACCTGCGG | 1800 |
| CCGCTGGAGG | TGCGGCGGGG | GCTGCGCGCC | CAGGCCTGCG | CCTTCTGGAA | CCGCTTCCTC | 1860 |
| CCCAAATTGC | TCAGCGCCAC | CGCCTCGGAG | GCTCCCAGCA | CCTGCCCAGG | CTTCACCCAT | 1920 |
| GGGGAGGCTG | CTCCGAGGCC | CGGCCTCCCC | CTGCCCCTCC | TCCTCCTCCA | CCAGCTTCTC | 1980 |
| CTCCTCTTCC | TCTCCCACCT | CCGGCGGCTG | TGAACACGGC | CTCTTCCCCT | ACGGCCTACA | 2040 |
| GGGGCCCCTC | CTCTAATGAG | TGGTAGGACC | TGTGGGAAG | GGCCCCACTC | AGGGATCTCA | 2100 |
| GACCTAGTGC | TCCCTTCCTC | CTCAAACCGA | GAGACTCACA | CTGGACAGGG | CAGGAGGAGG | 2160 |
| GGCCGTGCCT | CCCACCCTTC | TCAGGGACCC | CCACGCCTTT | GTTGTTTGAA | TGGAAATGGA | 2220 |
| AAAGCCAGTA | TTCTTTTATA | AAATTATCTT | TTGGAACCTG | AGCCTGACAT | TGGGGGAAGT | 2280 |
| GGAGGCCCGG | AAACGGGGTA | GCACCCCCAT | TGGGGCTATA | ACGGTCAACC | ATTTCTGTCT | 2340 |
| CTTCTTTTTC | CCCCAACCTC | CCCCTCCTGT | CCCCTCTGTT | CCCGTCTTCC | GGTCATTCTT | 2400 |
| TTCTCCTCCT | CTCTCCTTCC | TGCTGTCCTT | CTCGGCCCCG | CCTCTGCCCT | CATCCTCCCT | 2460 |
| CTCGTCTTTC | GCACATTCTC | CTGATCCTCT | TGCCACCGTC | CCACGTGGTC | GCCTGCATTT | 2520 |
| CTCCGTGCGT | CCTCCCTGCA | CTCATACCCC | CCCTTCAACC | CGCCCAAATG | TCCGATCCCC | 2580 |
| GACCTTCCTC | GTGCCGTCCT | CCCCTCCCGC | CTCGCTGGGC | GCCCTGGCCG | CAGACACGCT | 2640 |
| CGACACGCTC | GACGAGGCGG | AGCGCCAGTG | GAAGGCCGAG | TTCCACCGCT | GGAGCTCCTA | 2700 |
| CATGGTGCAC | TGGAAGAACC | AGTTCGACCA | CTACAGCAAG | CAGGATCGCT | GCTCAGACCT | 2760 |
| GTGACCCCGG | CGGGACCCCC | ATGTCCTCCG | CTCCGCCCGG | CCCCCTAGCT | GTATATACTA | 2820 |
| TTTATTTCAG | GGCTGGGCTA | TAACACAGAC | GAGCCCCAGA | CTCTGCCCAT | CCCCACCCCA | 2880 |
| CCCCGACGTC | CCCCGGGGCT | CCCGGTCCTC | TGGCATGTCT | TCAGGCTGAG | CTCCTCCCCG | 2940 |
| CGTGCCTTCG | CCCTCTGGCT | GCAAATAAAC | TGTTACAGGC | CAAAAAAAA | AAAAAAAAA | 3000 |
| AAAAAAAAAA | AAAAA | | | | | 3016 |

( 2 ) INFORMATION FOR SEQ ID NO:8:

( i ) SEQUENCE CHARACTERISTICS:
        ( A ) LENGTH: 2416 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
  ( A ) ORGANISM: Homo sapiens
  ( F ) TISSUE TYPE: Basal ganglion ( v i i i ) POSITION IN GENOME:
  ( B ) MAP POSITION: 3q26

( i x ) FEATURE:
  ( A ) NAME/KEY: mat_peptide
  ( B ) LOCATION: 214..1935
  ( D ) OTHER INFORMATION: /EC_number=3.1.1.8
    / gene="BCHE"
    / note= "butyrylcholinesterase mature peptide"

( i x ) FEATURE:
  ( A ) NAME/KEY: sig_peptide
  ( B ) LOCATION: 130..213

( i x ) FEATURE:
  ( A ) NAME/KEY: mRNA
  ( B ) LOCATION: 1..2416

( i x ) FEATURE:
  ( A ) NAME/KEY: CDS
  ( B ) LOCATION: 130..1938

( x i ) SEQUENCE DESCRIPTION: SEQ ID NO:8:

| | | | | | | |
|---|---|---|---|---|---|---|
| TACTGAATGT | CAGTGCAGTC | CAATTTACAG | GCTGGAGCAG | CAGCTGCATC | CTGCATTTCC | 6 0 |
| CCGAAGTATT | ACATGATTTT | CACTCCTTGC | AAACTTTACC | ATCTTTGTTG | CAGAGAATCG | 1 2 0 |
| GAAATCAATA | TGCATAGCAA | AGTCACAATC | ATATGCATCA | GATTTCTCTT | TTGGTTTCTT | 1 8 0 |
| TTGCTCTGCA | TGCTTATTGG | GAAGTCACAT | ACTGAAGATG | ACATCATAAT | TGCAACAAAG | 2 4 0 |
| AATGGAAAAG | TCAGAGGGAT | GAACTTGACA | GTTTTGGTG | GCACGGTAAC | AGCCTTTCTT | 3 0 0 |
| GGAATTCCCT | ATGCACAGCC | ACCTCTTGGT | AGACTTCGAT | TCAAAAAGCC | ACAGTCTCTG | 3 6 0 |
| ACCAAGTGGT | CTGATATTTG | GAATGCCACA | AAATATGCAA | ATTCTTGCTG | TCAGAACATA | 4 2 0 |
| GATCAAAGTT | TTCCAGGCTT | CCATGGATCA | GAGATGTGGA | ACCCAAACAC | TGACCTCAGT | 4 8 0 |
| GAAGACTGTT | TATATCTAAA | TGTATGGATT | CCAGCACCTA | AACCAAAAAA | TGCCACTGTA | 5 4 0 |
| TTGATATGGA | TTTATGGTGG | TGGTTTTCAA | ACTGGAACAT | CATCTTTACA | TGTTTATGAT | 6 0 0 |
| GGCAAGTTTC | TGGCTCGGGT | TGAAAGAGTT | ATTGTAGTGT | CAATGAACTA | TAGGGTGGGT | 6 6 0 |
| GCCCTAGGAT | TCTTAGCTTT | GCCAGGAAAT | CCTGAGGCTC | CAGGGAACAT | GGGTTTATTT | 7 2 0 |
| GATCAACAGT | TGGCTCTTCA | GTGGGTTCAA | AAAAATATAG | CAGCCTTTGG | TGGAAATCCT | 7 8 0 |
| AAAAGTGTAA | CTCTCTTTGG | AGAAAGTGCA | GGAGCAGCTT | CAGTTAGCCT | GCATTTGCTT | 8 4 0 |
| TCTCCTGGAA | GCCATTCATT | GTTCACCAGA | GCCATTCTGC | AAAGTGGATC | CTTTAATGCT | 9 0 0 |
| CCTTGGGCGG | TAACATCTCT | TTATGAAGCT | AGGAACAGAA | CGTTGAACTT | AGCTAAATTG | 9 6 0 |
| ACTGGTTGCT | CTAGAGAGAA | TGAGACTGAA | ATAATCAAGT | GTCTTAGAAA | TAAAGATCCC | 1 0 2 0 |
| CAAGAAATTC | TTCTGAATGA | AGCATTTGTT | GTCCCTATG | GGACTCCTTT | GTCAGTAAAC | 1 0 8 0 |
| TTTGGTCCGA | CCGTGGATGG | TGATTTTCTC | ACTGACATGC | CAGACATATT | ACTTGAACTT | 1 1 4 0 |
| GGACAATTTA | AAAAACCCA | GATTTGGTG | GGTGTTAATA | AAGATGAAGG | GACAGCTTTT | 1 2 0 0 |
| TTAGTCTATG | GTGCTCCTGG | CTTCAGCAAA | GATAACAATA | GTATCATAAC | TAGAAAAGAA | 1 2 6 0 |
| TTTCAGGAAG | GTTTAAAAAT | ATTTTTTCCA | GGAGTGAGTG | AGTTTGGAAA | GGAATCCATC | 1 3 2 0 |
| CTTTTTCATT | ACACAGACTG | GGTAGATGAT | CAGAGACCTG | AAAACTACCG | TGAGGCCTTG | 1 3 8 0 |
| GGTGATGTTG | TTGGGGATTA | TAATTTCATA | TGCCCTGCCT | TGGAGTTCAC | CAAGAAGTTC | 1 4 4 0 |

| | | | | | |
|---|---|---|---|---|---|
|TCAGAATGGG|GAAATAATGC|CTTTTTCTAC|TATTTTGAAC|ACCGATCCTC|CAAACTTCCG|1500
|TGGCCAGAAT|GGATGGGAGT|GATGCATGGC|TATGAAATTG|AATTTGTCTT|TGGTTTACCT|1560
|CTGGAAAGAA|GAGATAATTA|CACAAAAGCC|GAGGAAATTT|TGAGTAGATC|CATAGTGAAA|1620
|CGGTGGGCAA|ATTTTGCAAA|ATATGGGAAT|CCAAATGAGA|CTCAGAACAA|TAGCACAAGC|1680
|TGGCCTGTCT|TCAAAAGCAC|TGAACAAAAA|TATCTAACCT|TGAATACAGA|GTCAACAAGA|1740
|ATAATGACGA|AACTACGTGC|TCAACAATGT|CGATTCTGGA|CATCATTTTT|TCCAAAAGTC|1800
|TTGGAAATGA|CAGGAAATAT|TGATGAAGCA|GAATGGGAGT|GGAAAGCAGG|ATTCCATCGC|1860
|TGGAACAATT|ACATGATGGA|CTGGAAAAAT|CAATTTAACG|ATTACACTAG|CAAGAAAGAA|1920
|AGTTGTGTGG|GTCTCTAATT|AATAGATTTA|CCCTTTATAG|AACATATTTT|CCTTTAGATC|1980
|AAGGCAAAAA|TATCAGGAGC|TTTTTTACAC|ACCTACTAAA|AAAGTTATTA|TGTAGCTGAA|2040
|ACAAAAATGC|CAGAAGGATA|ATATTGATTC|CTCACATCTT|TAACTTAGTA|TTTTACCTAG|2100
|CATTTCAAAA|CCCAAATGGC|TAGAACATGT|TTAATTAAAT|TTCACAATAT|AAAGTTCTAC|2160
|AGTTAATTAT|GTGCATATTA|AAACAATGGC|CTGGTTCAAT|TTCTTTCTTT|CCTTAATAAA|2220
|TTTAAGTTTT|TTCCCCCCAA|AATTATCAGT|GCTCTGCTTT|TAGTCACGTG|TATTTTCATT|2280
|ACCACTCGTA|AAAAGGTATC|TTTTTAAAT|GAATTAAATA|TTGAAACACT|GTACACCATA|2340
|GTTTACAATA|TTATGTTTCC|TAATTAAAAT|AAGAATTGAA|TGTCAATATG|AGATATTAAA|2400
|ATAAGCACAG|AAAATC| | | | |2416

( 2 ) INFORMATION FOR SEQ ID NO:9:

( i ) SEQUENCE CHARACTERISTICS:
        ( A ) LENGTH: 2381 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( D ) DEVELOPMENTAL STAGE: fetal
        ( F ) TISSUE TYPE: Brain, Liver ( v i i i ) POSITION IN GENOME:
        ( B ) MAP POSITION: 3q26

( i x ) FEATURE:
        ( A ) NAME/KEY: mat_peptide
        ( B ) LOCATION: 160..1881
        ( C ) IDENTIFICATION METHOD: experimental
        ( D ) OTHER INFORMATION: /EC_number=3.1.1.8
            / evidence=EXPERIMENTAL
            / gene="BCHE"
            / note= "butyrylcholinesterase mature peptide"

( i x ) FEATURE:
        ( A ) NAME/KEY: sig_peptide
        ( B ) LOCATION: 76..159

( i x ) FEATURE:
        ( A ) NAME/KEY: mRNA
        ( B ) LOCATION: 1..2381

( i x ) FEATURE:
        ( A ) NAME/KEY: CDS
        ( B ) LOCATION: 76..1884

( x i ) SEQUENCE DESCRIPTION: SEQ ID NO:9:

-continued

| | | | | | |
|---|---|---|---|---|---|
| ATTTCCCCGA | AGTATTACAT | GATTTTCACT | CCTTGCAAAC | TTTGCCATCT | TGTTGCAGA | 60 |
| GAATCGGAAA | TCAATATGCA | TAGCAAAGTC | ACAATCATAT | GCATCAGATT | TCTCTTTTGG | 120 |
| TTTCTTTTGC | TCTGCATGCT | TATTGGGAAG | TCACATACTG | AAGATGACAT | CATAATTGCA | 180 |
| ACAAAGAATG | GAAAAGTCAG | AGGGATGAAC | TTGACAGTTT | TGGTGGCAC | GGTAACAGCC | 240 |
| TTTCTTGGAA | TTCCCTATGC | ACAGCCACCT | CTTGGTAGAC | TTCGATTCAA | AAAGCCACAG | 300 |
| TCTCTGACCA | AGTGGTCTGA | TATTTGGAAT | GCCACAAAAT | ATGCAAATTC | TTGCTGTCAG | 360 |
| AACATAGATC | AAAGTTTTCC | AGGCTTCCAT | GGATCAGAGA | TGTGGAACCC | AAACACTGAC | 420 |
| CTCAGTGAAG | ACTGTTTATA | TCTAAATGTA | TGGATTCCAG | CACCTAAACC | AAAAAATGCC | 480 |
| ACTGTATTGA | TATGGATTTA | TGGTGGTGGT | TTTCAAACTG | AACATCATC | TTTACATGTT | 540 |
| TATGATGGCA | AGTTCTGGC | TCGGGTTGAA | AGAGTTATTG | TAGTGTCAAT | GAACTATAGG | 600 |
| GTGGGTGCCC | TAGGATTCTT | AGCTTTGCCA | GGAAATCCTG | AGGCTCCAGG | GAACATGGGT | 660 |
| TTATTTGATC | AACAGTTGGC | TCTTCAGTGG | GTTCAAAAAA | ATATAGCAGC | CTTTGGTGGA | 720 |
| AATCCTAAAA | GTGTAACTCT | CTTTGGAGAA | AGTGCAGGAG | CAGCTTCAGT | TAGCCTGCAT | 780 |
| TTGCTTTCTC | CTGGAAGCCA | TTCATTGTTC | ACCAGAGCCA | TTCTGCAAAG | TGGATCCTTT | 840 |
| AATGCTCCTT | GGGCGGTAAC | ATCTCTTTAT | GAAGCTAGGA | ACAGAACGTT | GAACTTAGCT | 900 |
| AAATTGACTG | GTTGCTCTAG | AGAGAATGAG | ACTGAAATAA | TCAAGTGTCT | TAGAAATAAA | 960 |
| GATCCCCAAG | AAATTCTTCT | GAATGAAGCA | TTTGTTGTCC | CCTATGGGAC | TCCTTTGTCA | 1020 |
| GTAAACTTTG | GTCCGACCGT | GGATGGTGAT | TTTCTCACTG | ACATGCCAGA | CATATTACTT | 1080 |
| GAACTTGGAC | AATTTAAAAA | AACCCAGATT | TGGTGGGTG | TTAATAAAGA | TGAAGGGACA | 1140 |
| GCTTTTTTAG | TCTATGGTGC | TCCTGGCTTC | AGCAAAGATA | ACAATAGTAT | CATAACTAGA | 1200 |
| AAAGAATTTC | AGGAAGGTTT | AAAAATATTT | TTTCCAGGAG | TGAGTGAGTT | TGGAAAGGAA | 1260 |
| TCCATCCTTT | TTCATTACAC | AGACTGGGTA | GATGATCAGA | GACCTGAAAA | CTACCGTGAG | 1320 |
| GCCTTGGGTG | ATGTTGTTGG | GGATTATAAT | TCATATGCC | CTGCCTTGGA | GTTCACCAAG | 1380 |
| AAGTTCTCAG | AATGGGGAAA | TAATGCCTTT | TTCTACTATT | TTGAACACCG | ATCCTCCAAA | 1440 |
| CTTCCGTGGC | CAGAATGGAT | GGGAGTGATG | CATGGCTATG | AAATTGAATT | TGTCTTTGGT | 1500 |
| TTACCTCTGG | AAAGAAGAGA | TAATTACACA | AAAGCCGAGG | AAATTTTGAG | TAGATCCATA | 1560 |
| GTGAAACGGT | GGGCAAATTT | TGCAAAATAT | GGGAATCCAA | ATGAGACTCA | GAACAATAGC | 1620 |
| ACAAGCTGGC | CTGTCTTCAA | AAGCACTGAA | CAAAAATATC | TAACCTTGAA | TACAGAGTCA | 1680 |
| ACAAGAATAA | TGACGAAACT | ACGTGCTCAA | CAATGTCGAT | TCTGGACATC | ATTTTTTCCA | 1740 |
| AAAGTCTTGG | AAATGACAGG | AAATATTGAT | GAAGCAGAAT | GGGAGTGGAA | AGCAGGATTC | 1800 |
| CATCGCTGGA | ACAATTACAT | GATGGACTGG | AAAAATCAAT | TAACGATTA | CACTAGCAAG | 1860 |
| AAAGAAAGTT | GTGTGGGTCT | CTAATTAATA | GATTTACCCT | TTATAGAACA | TATTTTCCTT | 1920 |
| TAGATCAAGG | CAAAAATATC | AGGAGCTTTT | TTACACACCT | ACTAAAAAG | TTATTATGTA | 1980 |
| GCTGAAACAA | AAATGCCAGA | AGGATAATAT | TGATTCCTCA | CATCTTTAAC | TTAGTATTTT | 2040 |
| ACCTAGCATT | TCAAAACCCA | AATGGCTAGA | ACATGTTTAA | TTAAATTTCA | CAATATAAAG | 2100 |
| TTCTACAGTT | AATTATGTGC | ATATTAAAAC | AATGGCCTGG | TTCAATTTCT | TTCTTTCCTT | 2160 |
| AATAAATTTA | AGTTTTTTCC | CCCCAAAATT | ATCAGTGCTC | TGCTTTTAGT | CACGTGTATT | 2220 |

| | | | | | | |
|---|---|---|---|---|---|---|
| TTCATTACCA | CTCGTAAAAA | GGTATCTTTT | TTAAATGAAG | TTAAATATTG | AAACACTGTA | 2280 |
| CACCATAGTT | TACAATAATT | AGTGTTTCCT | AAGTTAAAAT | AAGAATTGAA | TGTCAATAAT | 2340 |
| GAGAATAATT | AAATAAGCA | CAGAAAATCA | CAAAAAAAA | C | | 2381 |

We claim:

1. A synthetic partially phosphorothioated antisense oligodeoxynucleotide directed against a region spanning the initiator AUG codon in the human ACHE gene, said oligodeoxynucleotide having the formula:

5'-CTGCGGGGGCCTCAT-3' (SEQ ID NO:2)

wherein said oligodeoxynucleotide has phosphorotioate bonds linking between the four 3'-terminus nucleotide bases.

2. The synthetic partially phosphorothioated oligodeoxynucleotide of claim 1 comprising SEQ ID No:2 which stimulates megakaryocytopoiesis.

3. The synthetic partially phosphorothioated oligodeoxynucleotide of claim 1 comprising SEQ ID No:2 which inhibits erythropoiesis during the first four days in vitro and ten days in vivo.

4. The synthetic partially phosphorothioated oligodeoxynucleotides of claim 1 comprising SEQ ID No:2 which diverts hemopoietic bone marrow cells development from megakaryocytes and erythrocytes to macrophages and mononuclear cells.

5. The synthetic partially phosphorothioated oligodeoxynucleotide of claim 1 comprising SEQ ID No:2 which increases in vitro hemopoietic stem cell fraction in bone marrow cells samples.

6. The synthetic partially phosphorothioated oligodeoxynucleotide according to claim 1 which enhances in vivo macrophage production and increasing hemopoietic stem cell counts.

7. A composition for increasing hemopoietic stem cell fraction in bone marrow cells samples in vitro wherein the composition comprises a partially phosphorothioated oligodeoxynucleotide according to claim 1.

8. A composition for enhancing macrophage production and increasing hemopoietic stem cell counts wherein the composition comprises a partially phosphorothioated oligodeoxynucleotide according to claim 1.

9. A composition for ex vivo reducing the immune response of organs to be transplanted wherein the composition comprises a synthetic partially phosphorothioated oligodeoxynucleotide according to claim 1.

10. A method of increasing stem cell fraction in bone marrow cells samples ex vivo to be transplanted by contacting a sample of extracted bone marrow with an effective amount of an oligodeoxynucleotide according to claim 1.

11. A method of treating embryonic or fetal bone marrow cells ex vivo prior to their storage in cell banks in viable forms devoid of tissue compatibility antigens, by contacting a sample with an effective amount of an oligodeoxynucleotide according to claim 1.

* * * * *